(12) United States Patent
Stewart et al.

(10) Patent No.: US 12,312,592 B2
(45) Date of Patent: May 27, 2025

(54) RETROVIRAL VECTOR

(71) Applicant: Oxford BioMedica (UK) Limited, Oxford (GB)

(72) Inventors: Hannah Stewart, Oxford (GB); Helen Maunder, Bicester (GB); Kyriacos Mitrophanous, Oxford (GB); Daniel Farley, Oxford (GB)

(73) Assignee: Oxford BioMedica (UK) Limited, Oxford (GB)

( * ) Notice: Subject to any disclaimer, the term of this patent is extended or adjusted under 35 U.S.C. 154(b) by 0 days.

(21) Appl. No.: 18/106,972

(22) Filed: Feb. 7, 2023

(65) Prior Publication Data

US 2023/0183745 A1 Jun. 15, 2023

Related U.S. Application Data

(63) Continuation of application No. 16/231,349, filed on Dec. 21, 2018, now abandoned.

(30) Foreign Application Priority Data

Dec. 22, 2017 (EP) .................................... 17210359

(51) Int. Cl.
*C12N 15/86* (2006.01)

(52) U.S. Cl.
CPC .... *C12N 15/86* (2013.01); *C12N 2740/10041* (2013.01); *C12N 2740/10052* (2013.01); *C12N 2740/13051* (2013.01); *C12N 2740/13052* (2013.01); *C12N 2740/15051* (2013.01); *C12N 2740/15052* (2013.01); *C12N 2740/16051* (2013.01); *C12N 2740/16052* (2013.01)

(58) Field of Classification Search
CPC .................................................... C12N 15/86
See application file for complete search history.

(56) References Cited

U.S. PATENT DOCUMENTS

| 2017/0145388 A1 | 5/2017 | Johnson et al. |
| 2020/0277629 A1 | 9/2020 | Cawood et al. |

FOREIGN PATENT DOCUMENTS

| EP | 0904392 B1 | 1/2001 |
| WO | WO 00/71678 A1 * | 11/2000 |
| WO | WO 2006/089001 A2 | 8/2006 |
| WO | WO 2012/028680 | 3/2012 |
| WO | WO 2012/028681 | 3/2012 |
| WO | WO 2013/043442 | 3/2013 |
| WO | WO 2015/092440 A1 * | 6/2015 |
| WO | WO 2016/189326 | 12/2016 |
| WO | WO 2017/017131 | 2/2017 |
| WO | WO 2017/089307 | 6/2017 |
| WO | WO 2017/089308 | 6/2017 |

OTHER PUBLICATIONS

Tolmacho et al., 2011 (Viral Gene Therapy, IntechOpen, Chapters/ 16787, p. 1-27).*
Geiling et al., A Modular Lentiviral and Retroviral Construction System to Rapidly Generate Vectors for Gene Expression and Gene Knockdown . . . , PLoS One 8:e76279 (2013).
Zhu et al., Multigene Lentiviral Vectors Based on Differential Splicing and Translational Control, Molecular Therapy, Oct. 2001, vol. 4, issue 4, pp. 375-382.
Moriarity et al., Modular assembly of transposon integratable multigen vectors using RecWay assembly, Nucleic Acids Research, 2013 vol. 41, No. 8, e92.
Osti et al., Comparative analysis of molecular strategies attenuating positional effects in lentiviral vectors carrying multiple genes, J. Virolog. Meth., 2006, 136:93-101.
Dunajova et al., Generation of stable packaging and producer cell lines for scalable lentiviral vector production, Poster.
Stornaiuolo et al,. RD2-MolPack-Chim3, a Packaging Cell Line for Stable Production of Lentiviral Vectors for Anti-HIV Gene Therapy, Hum. Gene Ther. Meth., 2013, 24:228-240.
Gossen et al., Tight control of gene expression in mammalian cells by tetracycline-responsive promoters, Proc. Natl. Acad. Sci., USA, Jun. 1992, vol. 89, pp. 5547-5551.
Stewart et al., Development of inducible EIAV-based lentviral vector packaging and producer cell lines, Gene Therapy, 2009 vol. 16, pp. 805-814.
Trinklein et al., An Abundance of Bidirectional Promoters in the Human Genome, Genome Research, 2004 14:62-66.
Trinklein et al., An Abundance of Bidirectional Promoters in the Human Genome, Genome Research, 2004 14: Suppl. Fig. 1-4.
Chen et al., Rapid Lentiviral Vector Producer Cell Line Generation Using a Single DNA Construct; Mol. Ther: Meth. Clin. Devel. 19:47-57; 2020.
Yao et al., Tetracycline Repressor, tetR, rather than the tetR-Mammalian Cell Transcription Factor Fusion Derivatives, Regulates . . . ; Human Gene Ther. 9:1939-50; 1998.

* cited by examiner

*Primary Examiner* — Anoop K Singh
*Assistant Examiner* — David A Montanari
(74) *Attorney, Agent, or Firm* — Grimes & Yvon LLP

(57) ABSTRACT

A cell for producing retroviral vectors comprising nucleic acid sequences encoding: i) gag-pol; ii) env; iii) the RNA genome of the retroviral vector; and iv) optionally rev, or a functional substitute thereof, wherein at least two nucleic acid sequences are located at the same genetic locus; and wherein the at least two nucleic acid sequences are in reverse and/or alternating orientations.

12 Claims, 10 Drawing Sheets

| Plasmid Names | Modular Construct ID | Diagram | Average GFP FACS titres (TU/ml) |
|---|---|---|---|
| pPC-T-VSVG-T-HRev-Zeo pOXB.TetO2HSGP.Bsr pPCL-HVCG-Hyg | MO3 | VSV-G → ← HRev Genome → GagPol → | 4.9E+05 |
| pPC-T-GagPol-T-HRevHyg pPC-T-VSVG-Zeo pPCL-HVCG-Hyg | MO4 | GagPol ← ← HRev Genome → VSV-G → | 2.8E+06 |
| pPC-T-GagPol-T-VSVG-T-HRev-Zeo pPCL-HVCG-Hyg | MO5 | GagPol | VSV-G × ← HRev Genome → | 3.1E+06 |
| pPCL-HVCG-T-GagPol-T-HRev-T-VSVG-Hyg | MO6 | Genome → GagPol → VSV-G → ← HRev | 4.1E+04 |
| pPCL-HVCG-HRev-IRES-Bsr pOXB.TetO2.HSGP.Bsr pPC-T-VSVG-Zeo | MO11 | Genome → GagPol × HRev-IRES VSV-G → | 8.3E+05 |
| pPC-T-VSVG-HRev-IRES-Zeo pOXB.TetO2.HSGP.Bsr pPCL-HVCG-Hyg | MO12 | Genome → VSV-G × HRev-IRES GagPol → | 1.7E+06 |
| pPC-T-GagPol-T-HRev-IRES-Hyg pPC-T-VSVG-Zeo pPCL-HVCG-Hyg | MO13 | Genome → GagPol × HRev-IRES GagPol → | 2.5E+06 |

| Plasmids | Name | Construct | Titer |
|---|---|---|---|
| pPC-T-GagPol-T-VSVG-HRev-IRES-Zeo<br>pPCL-HVCG-Hyg | MO14 | Genome → ← GagPol │ VSV-G ✕ HRev-IRES | 7.4E+05 |
| pPCL-HVCG-T-GagPol-T-VSVG-HRev-IRES-Zeo | MO15 | Genome → ← GagPol │ VSV-G ✕ HRev-IRES | 2.6E+05 |
| pPC-T-GagPol-T-VSVG-Zeo<br>pPCL-HVCG-Hyg<br>pPC-T-Hrev | MO20 | Genome → ← GagPol │ VSV-G ↑ HRev | 2.5E+07 |
| pPCL-HVCG-T-HRev-Hyg<br>POXB.TetO2HSGP.Bsr<br>pPC-T-VSVG-Zeo | MO21 | GagPol → ← Genome │ HRev ↑ VSV-G | 1.4E+06 |

| Stably Transfected Plasmids | Strategy ID | Diagram (not to scale) | Pool Titre (GFP FACS) TU/ml |
|---|---|---|---|
| pOXB.TetO2.HSGP.Bsr<br>pPC-T-VSVG-Zeo<br>pPC-T-HRev | PAC001 | | 5.2E+03 |
| pPC-T-GagPol-T-VSVG-T-HRev-Zeo (MO5) | PAC002 | | 1.0E+03 |
| pPC-T-VSVG-T-HRev-Zeo (MO3)<br>pOXB.TetO2.HSGP.Bsr | PAC004 | | 9.4E+03 |
| pPC-T-GagPol-T-VSVG-HRev-IRES-Zeo (MO14) | PAC005 | | 2.0E+03 |
| pPC-T-GagPol-T-VSVG-Zeo (MO20) | PAC006 | | 5.6E+03 * |
| pPC-T-VSVG-T-HRev-Zeo (MO3)<br>pOXB.TetO2.HSGP.Bsr | PAC009 | | 4.5E+03 |

\* To screen this stable pool of packaging cells for LV production both Genome and Rev were transiently transfected (Rev was not stably transfected)

| Stably Transfected Plasmid Names | Modular Construct ID | Diagram (not to scale) | GPF FACS Titres (TU/ml) |
|---|---|---|---|
| pPC-T-VSVG-T-HRev-Zeo<br>pPCL-HVCG-Hyg<br>pOXB.TetO2.HSGP.Bsr | MO3 | VSV-G, HRev, Genome, GagPol | 2.4E+05 |
| pPC-T-VSVG-HRev-IRES-Zeo<br>pPCL-HVCG-Hyg<br>pOXB.TetO2.HSGP.Bsr | MO12 | VSV-G, HRev-IRES, Genome, GagPol | 1.19E+05 |
| pPCL-HVCG-T-HRev-Bsr<br>pPC-T-GagPol-T-VSVG-Zeo | MO1<br>MO20 | Genome, HRev, GagPol, VSV-G | 8.24E+04 |
| pPCL-HVCG-Hrev-IRES-Bsr<br>pPC-T-GagPol-T-VSVG-Zeo | MO11<br>MO20 | Genome, HRev-IRES, GagPol, VSV-G | 8.29E+04 |
| pPC-T-GagPol-T-VSVG-T-HRev-Zeo<br>pPCL-HVCG-Hvg | MO5 | GagPol, VSV-G, HRev, Genome | 7.06E+04 |
| pPC-T-GagPol-T-VSVG-HRev-IRES-Zeo<br>pPCL-HVCG-Hvg | MO14 | GagPol, VSV-G, Genome, HRev-IRES | 7.38E+04 |
| Single component constructs:<br>pPCL-HVCG-Hyg<br>pOXB.TetO2.HSGP.Bsr<br>pPC-T-Hrev<br>pPC-T-VSVG-Zeo | N/A | Genome, HRev, VSV-G, GagPol | 1.37E+05 |

FIG. 8

RETROVIRAL VECTOR

CROSS-REFERENCE TO RELATED APPLICATIONS

This application is a continuation of pending U.S. application Ser. No. 16/231,349, filed on Dec. 21, 2018, which claims the benefit of priority of expired European Patent Application No. 17210359.0, filed on Dec. 22, 2017, the entire contents of which are incorporated by reference herein.

FIELD OF THE INVENTION

The invention relates to the production of retroviral vectors. In particular, it relates to modular constructs comprising retroviral gene components.

BACKGROUND TO THE INVENTION

Gene therapy broadly involves the use of genetic material to treat disease. It includes the supplementation of cells with defective genes (e.g. those harbouring mutations) with functional copies of those genes, the inactivation of improperly functioning genes and the introduction of new therapeutic genes.

Therapeutic genetic material may be incorporated into the target cells of a host using vectors to enable the transfer of nucleic acids. Such vectors can be generally divided into viral and non-viral categories.

Viruses naturally introduce their genetic material into target cells of a host as part of their replication cycle. Engineered viral vectors harness this ability to enable the delivery of a nucleotide of interest (NOI) to a target cell. To date, a number of viruses have been engineered as vectors for gene therapy. These include retroviruses, adenoviruses (AdV), adeno-associated viruses (AAV), herpes simplex viruses (HSV) and vaccinia viruses.

In addition to modification to carry a nucleotide of interest, viral vectors are typically further engineered to be replication defective. As such, the recombinant vectors can directly infect a target cell, but are incapable of producing further generations of infective virions. Other types of viral vectors may be conditionally replication competent within cancer cells only, and may additionally encode a toxic transgene or pro-enzyme.

Retroviral vectors have been developed as therapies for various genetic disorders and are now showing increasing promise in clinical trials. Currently there are over 459 human clinical trials involving retroviral gene therapy registered in the Journal of Gene Medicine database; 158 gene therapy clinical trials are using lentiviral vectors (http://www.abedia.com/wiley/vectors.php, updated in April, 2017). Strimvelis received marketing authorisation from the European Commission on 26 May 2016; Strimvelis is a product for treatment of ADA-SCID based on patient CD34+ cells transduced ex vivo with retroviral vectors expressing the ADA gene. Kymriah (USAN: tisagenlecleucel) received approval from the FDA on 30 Aug. 2017; Kymriah is a product for the treatment of patients up to 25 years old with refractory ALL. Papers on retroviral gene therapy include Wang X, Naranjo A, Brown C E, Bautista C, Wong C W, Chang W C, Aguilar B, Ostberg J R, Riddell S R, Forman S J, Jensen M C (2012) J Immunother. 35(9):689-701, Hu Y, Wu Z, Luo Y, Shi J, Yu J, Pu C, Liang Z, Wei G, Cui Q, Sun J, Jiang J, Xie J, Tan Y, Ni W, Tu J, Wang J, Jin A, Zhang H, Cai Z, Xiao L, Huang H. (2017) Clin Cancer Res. 23(13):3297-3306, Galy, A. and A. J. Thrasher (2010) Curr Opin Allergy Clin Immunol 11(6): 545-550; Porter, D. L., B. L. Levine, M. Kalos, A. Bagg and C. H. June (2011) N Engl J Med 365(8): 725-733; Campochiaro, P. A. (2012) Gene Ther 19(2): 121-126; Cartier, N., S. Hacein-Bey-Abina, C. C. Bartholomae, P. Bougneres, M. Schmidt, C. V. Kalle, A. Fischer, M. Cavazzana-Calvo and P. Aubourg (2012) Methods Enzymol 507: 187-198; Sadelain, M., I. Riviere, X. Wang, F. Boulad, S. Prockop, P. Giardina, A. Maggio, R. Galanello, F. Locatelli and E. Yannaki (2010) Ann N Y Acad Sci 1202: 52-58; DiGiusto, D. L., A. Krishnan, L. Li, H. Li, S. Li, A. Rao, S. Mi, P. Yam, S. Stinson, M. Kalos, J. Alvarnas, S. F. Lacey, J. K. Yee, M. Li, L. Couture, D. Hsu, S. J. Forman, J. J. Rossi and J. A. Zaia (2010) Sci Transl Med 2(36): 36ra43 and Segura M M, M. M., Gaillet B, Garnier A. (2013) Expert opinion in biological therapy).

Important examples of such vectors include the gamma-retrovirus vector system (based on MMLV), the primate lentivirus vector system (based on HIV-1) and the non-primate lentivirus vector system (based on EIAV).

Reverse genetics has allowed these virus-based vectors to be heavily engineered such that vectors encoding large heterologous sequences (circa 10 kb) can be produced by transfection of mammalian cells with appropriate DNA sequences (reviewed in Bannert, K. (2010) Caister Academic Press: 347-370).

Engineering and use of retroviral vectors at the research stage typically involves the production of reporter-gene vectors encoding, for example, GFP or lacZ. The titres of these clinically irrelevant vectors are usually in the region of $1\times10^6$ to $1\times10^7$ transducing units per mL (TU/mL) of crude harvest material.

A common method to produce viral vectors is known as transient transfection. That is, viral genes necessary for the production of viral vectors are introduced into a host cell (for example, HEK-293) via plasmids by transfection. Furthermore, it is common for each component required for vector production to be encoded on separate plasmids. This is at least partly for safety reasons, as it would then require a number of recombination events to occur for a replication competent virus particle to be formed through the production process.

However, such a transient process has inherent drawbacks. The cost of transfection agents and plasmids are high, and coupled with the labour-intensive nature of the transfection technique, this makes transient transfection an expensive and technically complex process for clinical/commercial vector production.

Thus, there is a desire in the art to provide alternative methods of producing viral vectors which help to address the known issues associated with the transient transfection process.

There has been an attempt to generate stable packaging cell lines in recent years, where viral packaging genes are introduced into eukaryotic host cells along with selection markers such that these genes can be stably integrated into the cell. Similarly, stable producer cell lines also exist where the retroviral genome is also stably integrated. Both of these allow circumvention of a significant portion of the transient transfection process.

However, packaging and producer cell lines are difficult to generate in part due to the general requirement of sequentially introducing viral genetic components into the host cell. The difficulty of predicting the site of integration can also lead to unpredictable expression levels as well as genetic instability.

Another recently developed way of making packaging and producer cell lines is described in WO 2017/089308. It involves the use of nucleic acid vectors comprising a non-mammalian origin of replication such as bacterial artificial chromosomes, comprising the retroviral genes essential for retroviral vector production. Bacterial artificial chromosomes or "BAC" refers to a DNA construct derived from bacterial plasmids which is able to hold a large insert of exogenous DNA. They can usually hold a maximum DNA insert of approximately 350 kb. BACs were developed from the well characterised bacterial functional fertility plasmid (F-plasmid) which contains partition genes that promote the even distribution of plasmids after bacterial cell division. This allows the BACs to be stably replicated and segregated alongside endogenous bacterial genomes. The BAC usually contains at least one copy of an origin of replication (such as the oriSox or/Vgene), the repE gene (for plasmid replication and regulation of copy number) and partitioning genes which ensures stable maintenance of the BAC in bacterial cells. BACs are naturally circular and supercoiled which makes them easier to recover than linear artificial chromosomes.

Thus, there is a desire to improve both transient vector production as well as the process for generating stable packaging and producer cell lines.

SUMMARY OF THE INVENTION

The present inventors have found that surprisingly, modular constructs comprising at least two of the nucleic acid components necessary for viral vector production can be effective in generating vector production cells. In particular, this has been shown to be true for the use of bacterial plasmid constructs. The modular constructs of the present invention can be used for the generation of both transient and stable vector production cells.

Previously, it had been thought that this would be ineffective due to modular constructs, such as those of the present invention, being too large to be held by bacterial plasmids which were to be used for retroviral production, as oversized plasmids can lead to both genetic instability and poor expression. Additionally, the size of these constructs could negate the efficiency of cellular entry in transient and stable vector production systems, and integration in stable vector production cells using typical transfection methods. The safety and efficacy of using such plasmids for the generation of vector production cells could also be questioned as it may lead to an increased chance of the formation of replication-competent viral particles.

However, the present inventors have shown that modular constructs comprising at least two of the nucleic acid components necessary for viral vector production can be used to provide levels of vector production comparable to those with a traditional multi-plasmid transient process, but allowing for a significant reduction in, for example, the use of transfection agents. The inventors have shown that vector production does not appear to be significantly affected by the use of alternating orientations of the retroviral genes in the modular constructs. Furthermore, the retroviral genes in the modular constructs can be arranged in any order. Such modular constructs can also be used to evaluate the optimal stoichiometry of the various retroviral vector components to yield the most advantageous vector production cell.

As the modular constructs of the present invention contain two or more of the retroviral components on one construct, the safety profile of these modular constructs has been considered and additional safety features directly engineered into the invention. These features include the use of insulators for multiple open reading frames of retroviral vector components and the specific orientation and arrangement of the retroviral genes in the modular constructs. The inventors believe that by using these features the direct read-through to generate replication-competent viral particles will be prevented. The inventors have shown that the use of these features does not significantly impact the generation of viral vector in either transient or stable vector production systems.

The inventors have shown that the use of such modular constructs can allow for a more efficient process for the generation of stable packaging (PaCL) and producer cell lines (PCL). The use of modular constructs improves this process as multiple retroviral components are present on the same construct. Fewer constructs are required to be stably transfected into the host cell line and therefore fewer integration events are needed to occur to generate a stable PaCL/PCL. This significantly reduces production time and costs and also offers the advantage of reducing the number of selectable markers and thus selection steps required for stable cell line generation. With regard to the latter, this is particularly relevant as there are only a limited number of selectable markers available.

The fact that at least some (if not all) of the components necessary for vector production will be integrated at the same site within the production cell genome can further mean that such a process can also overcome problems such as gene silencing, which can occur when retroviral vector genes are integrated randomly and at different locations within the production cell genome.

Therefore, in one aspect, the present invention provides a cell for producing retroviral vectors comprising nucleic acid sequences encoding:
  i) gag-pol;
  ii) env;
  iii) optionally the RNA genome of the retroviral vector; and
  iv) optionally rev, or a functional substitute thereof,
  wherein at least two nucleic acid sequences are located at the same genetic locus in the genome of the cell; wherein the at least two nucleic acid sequences are in reverse and/or alternating orientations; and wherein the nucleic acid sequences encoding gag-pol and/or env are associated with at least one regulatory element.

In a further aspect, the present invention provides a cell for producing retroviral vectors comprising nucleic acid sequences encoding:
  i) gag-pol;
  ii) env;
  iii) optionally the RNA genome of the retroviral vector; and
  iv) rev, or a functional substitute thereof, wherein at least two nucleic acid sequences are located at the same genetic locus in the genome of the cell; and wherein the nucleic acid sequences encoding rev and env are in reverse and/or alternating orientations.

In a further aspect, the present invention provides a transient production cell for producing retroviral vectors comprising nucleic acid sequences encoding:
  i) gag-pol;
  ii) env;
  iii) optionally the RNA genome of the retroviral vector; and
  iv) rev, or a functional substitute thereof,
  wherein at least two nucleic acid sequences are located at the same genetic locus in the genome of the cell; and wherein the nucleic acid sequences encoding gag-pol and rev are in reverse and/or alternating orientations.

In a further aspect, the present invention provides a cell for producing retroviral vectors comprising nucleic acid sequences encoding:
i) gag-pol;
ii) env;
iii) optionally the RNA genome of the retroviral vector; and
iv) optionally rev, or a functional substitute thereof, wherein the nucleic acid sequences are located at, at least, two different loci within the cell, further wherein at least two nucleic acid sequences are located at the same genetic locus in the genome of the cell; and wherein the nucleic acid sequences encoding gag-pol and/or env are associated with at least one regulatory element.

In a further aspect, the present invention provides a cell for producing retroviral vectors comprising nucleic acid sequences encoding:
i) gag-pol;
ii) env;
iii) optionally the RNA genome of the retroviral vector; and
iv) rev, or a functional substitute thereof, wherein the nucleic acid sequences are located at, at least, two different loci within the cell, further wherein at least two nucleic acid sequences are located at the same genetic locus in the genome of the cell; and wherein the nucleic acid sequences encoding rev and env are in reverse and/or alternating orientations.

In a further aspect, the present invention provides a modular construct comprising at least two nucleic acid sequences selected from nucleic acid sequences encoding:
i) gag-pol;
ii) env;
iii) the RNA genome of the retroviral vector; and/or
iv) rev, or a functional substitute thereof;

wherein the at least two nucleic acid sequences are in reverse and/or alternating orientations; and wherein:
a) when the modular construct comprises a nucleic acid sequence encoding gag-pol, said nucleic acid sequence encoding gag-pol is associated with at least one regulatory element; or
b) when the modular construct comprises a nucleic acid sequence encoding env, said nucleic acid sequence encoding env is associated with at least one regulatory element; or
c) when the modular construct comprises nucleic acid sequences encoding gag-pol and env, said nucleic acid sequences encoding gag-pol and env are associated with at least one regulatory element.

In a further aspect, the present invention provides a modular construct comprising at least two nucleic acid sequences selected from nucleic acid sequences encoding:
i) gag-pol;
ii) env;
iii) the RNA genome of the retroviral vector; and/or
iv) rev or a functional substitute thereof;

wherein the modular construct does not contain a sequence derived from a PAC, BAC, YAC, cosmid or fosmid; and wherein:
a) when the modular construct comprises a nucleic acid sequence encoding gag-pol, said nucleic acid sequence encoding gag-pol is associated with at least one regulatory element; or
b) when the modular construct comprises a nucleic acid sequence encoding env, said nucleic acid sequence encoding env is associated with at least one regulatory element; or
c) when the modular construct comprises nucleic acid sequences encoding gag-pol and env, said nucleic acid sequences encoding gag-pol and env are associated with at least one regulatory element.

In a further aspect, the present invention provides a modular construct comprising nucleic acid sequences encoding env and rev, or a functional substitute thereof, in reverse and/or alternating orientations, and optionally nucleic acid sequences encoding gag-pol and/or the RNA genome of the retroviral vector.

In a further aspect, the present invention provides a modular construct comprising nucleic acid sequences encoding env and rev, or a functional substitute thereof, in reverse and/or alternating orientations, and optionally nucleic acid sequences encoding gag-pol and/or the RNA genome of the retroviral vector, wherein the modular construct does not contain a sequence derived from a PAC, BAC, YAC, cosmid or fosmid.

In a further aspect, the present invention provides a cell for producing retroviral vectors comprising at least one modular construct of the invention.

In a further aspect, the present invention provides a method for generating a production cell for producing retroviral vectors, comprising the steps of:
a) introducing at least one modular construct of the invention into a mammalian cell; and
b) optionally selecting for a mammalian cell which has the at least two nucleic acid sequences integrated within its genome.

In a further aspect, the present invention provides a method for generating a stable cell for producing retroviral vectors, comprising the steps of:
a) introducing at least one modular construct of the invention into a mammalian cell; and
b) selecting for a mammalian cell which has the at least two nucleic acid sequences integrated within its genome.

In a further aspect, the present invention provides a stable cell for producing retroviral vectors produced by a method of the invention.

In a further aspect, the present invention provides a method for generating a transient production cell for producing retroviral vectors, comprising introducing at least one modular construct of the invention into a mammalian cell.

In a further aspect, the present invention provides a transient production cell for producing retroviral vectors produced by a method of the invention.

In a further aspect, the present invention provides a method for producing a replication defective retroviral vector, comprising the steps of:
a) introducing a modular construct of the invention into a mammalian cell;
b) selecting for a mammalian cell which has the at least two nucleic acid sequence integrated within its genome
c) optionally introducing a nucleic acid vector which is different to the modular construct into the selected mammalian cell;
d) further culturing the mammalian cell under conditions in which the replication defective retroviral vector is produced; and
and optionally e) isolating the replication defective retroviral vector.

In a further aspect, the present invention provides a method for producing a replication defective retroviral vector, comprising the steps of:
a) introducing a modular construct of the invention into a mammalian cell;
b) optionally introducing a nucleic acid vector which is different to the modular construct into the mammalian cell; and
c) further culturing the mammalian cell under conditions in which the replication defective retroviral vector is produced;
and optionally d) isolating the replication defective retroviral vector.

In a further aspect, the present invention provides a replication defective retroviral vector produced by any method of the invention.

DESCRIPTION OF THE FIGURES

FIG. 5. Different combinations of LV modular constructs were tested for their ability to generate LV-GFP following transient co-transfection of HEK293T.TetR14 cells (which constitutively express the TetR protein). Here is shown the schematic of each of the modular constructs that were tested and the average GFP FACS titre (TU/ml) of the resulting vector following transient co-transfection of HEK293T cells with each of the modular constructs plus remaining single component plasmids to complete the vector production system.

FIG. 6. Stable pools of packaging cells were generated by stable transfection using different combinations of single or modular LV constructs followed by a period of antibiotic selection. Resulting stable packaging cells were tested for their ability to generate LV-GFP following transient transfection of HIV-1 GFP genome (and Rev for PAC006) and doxycycline induction of the cell line. Here is shown the schematic of each of the modular constructs and single plasmids that were used to generate pools of stable packaging cells. Also shown are the resulting GFP FACS titres (TU/ml) of the LV GFP vector that was produced from each pool of packaging cells following transient transfection of HIV-1 GFP genome (and HIV-1 Rev for PAC006) and doxycycline induction.

FIG. 8. Stable pools of producer cells were generated by stable transfection using different combinations of single plasmids or modular LV constructs followed by a period of antibiotic selection. Resulting producer cell lines were tested for their ability to generate LV-GFP following doxycycline induction of the cell line. Here is shown the schematic of each of the modular plasmids that were evaluated and the average GFP FACS titre (TU/ml) of the resulting vector following doxycycline induction.

DETAILED DESCRIPTION OF THE INVENTION

Figure 1:
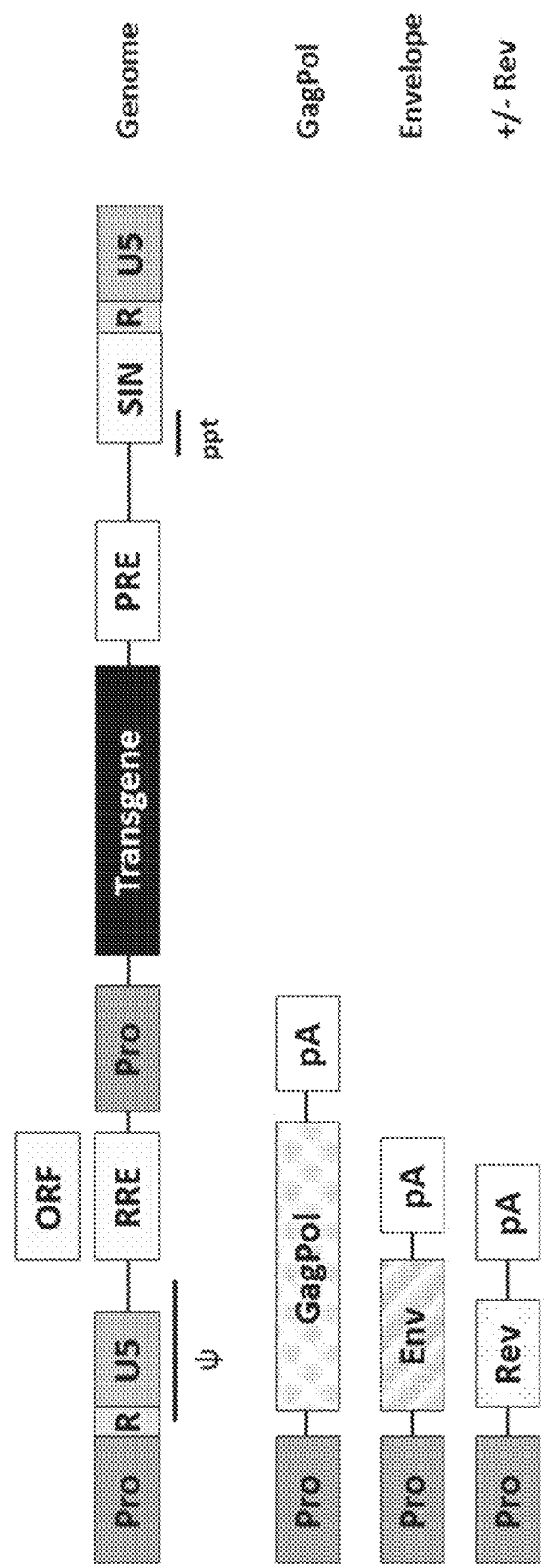
FIG. 1: (A) A schematic displaying typical retroviral vector components. The therapeutic retroviral vector systems currently used have been highly engineered from the wild-type virus genomes from which they were derived. Gamma-retroviral vectors are typically produced using 3- or 4-component systems requiring vector genome, Gag/Pol and envelope expression constructs and, for a number of lentiviral vector systems, the accessory gene Rev is also required. EIAV-based lentiviral vectors do not require Rev if an open-reading frame (ORF) replaces RRE. Vector genomes typically require a packaging signal ($\psi$), a nucleotide of interest (NOI), (optionally) a post-transcriptional element (PRE), the 3'ppu and a self-inactivating (SIN) LTR. The R-U5 regions are required for correct polyadenylation of both vector genome RNA and transgene mRNA, as well as the process of reverse transcription. Usually both 'external' and 'internal' promoters (Pro) encoded within the genome cassette are strong eukaryotic or virus promoters, as are those driving the other vector system components.

The practice of the present invention will employ, unless otherwise indicated, conventional techniques of chemistry, molecular biology, microbiology and immunology, which are within the capabilities of a person of ordinary skill in the art. Such techniques are explained in the literature. See, for example, J. Sambrook, E. F. Fritsch, and T. Maniatis (1989) Molecular Cloning: A Laboratory Manual, Second Edition, Books 1-3, Cold Spring Harbor Laboratory Press; Ausubel, F. M. et al. (1995 and periodic supplements) Current Protocols in Molecular Biology, Ch. 9, 13, and 16, John Wiley & Sons, New York, NY; B. Roe, J. Crabtree, and A. Kahn (1996) DNA Isolation and Sequencing: Essential Techniques, John Wiley & Sons; J. M. Polak and James O'D. McGee (1990) In Situ Hybridization: Principles and Practice; Oxford University Press; M. J. Gait (ed.) (1984) Oligonucleotide Synthesis: A Practical Approach, IRL Press; and, D. M. J. Lilley and J. E. Dahlberg (1992) Methods of Enzymology: DNA Structure Part A: Synthesis and Physical Analysis of DNA Methods in Enzymology, Academic Press.

All of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

Unless defined otherwise, all technical and scientific terms used herein have the same meaning as is commonly understood by one of skill in the art to which this invention belongs. Unless otherwise specified, "rev" and "gag-pol" refer to the proteins and/or genes of lentiviral vectors.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Wherever embodiments are described with the language "comprising," otherwise analogous embodiments described in terms of "consisting of" and/or "consisting essentially of" are included.

Units, prefixes, and symbols are denoted in their Systeme International de Unites (SI) accepted form. Numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth. Likewise, a disclosed range is a disclosure of each individual value encompassed by the range. For example, a stated range of 5-10 is also a disclosure of 5, 6, 7, 8, 9, and 10.

Vectors

The present invention relates to retroviral vectors.

A vector is a tool that allows or facilitates the transfer of an entity from one environment to another. In accordance with the present invention, and by way of example, some vectors used in recombinant nucleic acid techniques allow entities, such as a segment of nucleic acid (e.g. a heterologous DNA segment, such as a heterologous cDNA segment), to be transferred into and expressed by a target cell. The vector may facilitate the integration of the nucleic acid/nucleotide of interest (NOI) to maintain the NOI and its expression within the target cell. Alternatively, the vector may facilitate the replication of the vector through expression of the NOI in a transient system.

The vectors of the invention are viral vectors, in particular retroviral vectors, with a promoter for the expression of the said NOI and optionally a regulator of the NOI. The vectors may contain one or more selectable marker genes (e.g. a neomycin resistance gene) and/or traceable marker gene(s) (e.g. a gene encoding green fluorescent protein (GFP)). Vectors may be used, for example, to infect and/or transduce a target cell.

The retroviral vector may be used to replicate the NOI in a compatible target cell in vitro. Thus, the invention provides a method of making proteins in vitro by introducing a vector of the invention into a compatible target cell in vitro and growing the target cell under conditions which result in expression of the NOI. Protein and NOI may be recovered from the target cell by methods well known in the art. Suitable target cells include mammalian cell lines and other eukaryotic cell lines.

The vector may be an expression vector. Expression vectors as described herein comprise regions of nucleic acid containing sequences capable of being transcribed. Thus, sequences encoding mRNA, tRNA and rRNA are included within this definition.

In some aspects the vectors may have "insulators"—genetic sequences that block the interaction between promoters and enhancers, and act as a barrier reducing read-through from an adjacent gene.

In one embodiment the insulator is present between one or more of the retroviral nucleic acid sequences to prevent promoter interference and read-thorough from adjacent genes. If the insulators are present in the modular construct between one or more of the retroviral nucleic acid sequences, then each of these insulated genes may be arranged as individual expression units.

In nature, open reading frames (ORF—a continuous stretch of codons which can be translated into proteins) can exist in forward and reverse orientations. This strategy is used by organisms, such as viruses, to increase their genetic diversity whilst limiting the overall size of their genome. In this instance, the reverse and/or alternating orientations refers to the spatial configuration of the expression cassettes within the modular plasmid. Usually modular plasmids are constructed in a spatial arrangement where expression cassettes are arranged 'head-to-tail' orientation. The modular plasmids described here are spatially arranged where the expression cassettes can be arranged in spatially opposing orientations such as 'tail-to-tail' and 'head-to-head'. Whilst each expression cassette has its own promoter and polyA regions, the use of such orientations prevents the collision of replication and transcription complexes and additionally prevents the generation of aberrant transcripts due to transcriptional read-through.

In one aspect, the present invention provides a cell for producing retroviral vectors comprising nucleic acid sequences encoding:

i) gag-pol;

ii) env;

iii) optionally the RNA genome of the retroviral vector; and iv) optionally rev, or a functional substitute thereof, wherein at least two nucleic acid sequences are located at the same genetic locus in the genome of the cell; wherein the at least two nucleic acid sequences are in reverse and/or alternating orientations; and wherein the nucleic acid sequences encoding gag-pol and/or env are associated with at least one regulatory element.

In a further aspect, the present invention provides a cell for producing retroviral vectors comprising nucleic acid sequences encoding:

i) gag-pol;

ii) env;

iii) optionally the RNA genome of the retroviral vector; and iv) rev, or a functional substitute thereof, wherein at least two nucleic acid sequences are located at the same genetic locus in the genome of the cell; and wherein the nucleic acid sequences encoding rev and env are in reverse and/or alternating orientations.

In a further aspect, the present invention provides a transient production cell for producing retroviral vectors comprising nucleic acid sequences encoding:
i) gag-pol;
ii) env;
iii) optionally the RNA genome of the retroviral vector; and
iv) rev, or a functional substitute thereof,
wherein at least two nucleic acid sequences are located at the same genetic locus in the genome of the cell; and wherein the nucleic acid sequences encoding gag-pol and rev are in reverse and/or alternating orientations.

In a further aspect, the present invention provides a cell for producing retroviral vectors comprising nucleic acid sequences encoding:
i) gag-pol;
ii) env;
iii) optionally the RNA genome of the retroviral vector; and
iv) optionally rev, or a functional substitute thereof,
wherein the nucleic acid sequences are located at, at least, two different loci within the cell, further wherein at least two nucleic acid sequences are located at the same genetic locus in the genome of the cell; and wherein the nucleic acid sequences encoding gag-pol and/or env are associated with at least one regulatory element.

In a further aspect, the present invention provides a cell for producing retroviral vectors comprising nucleic acid sequences encoding:
i) gag-pol;
ii) env;
iii) optionally the RNA genome of the retroviral vector; and
iv) rev, or a functional substitute thereof,
wherein the nucleic acid sequences are located at, at least, two different loci within the cell, further wherein at least two nucleic acid sequences are located at the same genetic locus in the genome of the cell; and wherein the nucleic acid sequences encoding rev and env are in reverse and/or alternating orientations.

In another embodiment, the retrovirus is derived from a foamy virus.

In another embodiment, the retroviral vector is derived from a lentivirus.

In another embodiment, the lentiviral vector is derived from HIV-1, HIV-2, SIV, FIV, BIV, EIAV, CAEV or Visna lentivirus.

Retroviral and Lentiviral Vectors

The retroviral vector of the present invention may be derived from or may be derivable from any suitable retrovirus. A large number of different retroviruses have been identified. Examples include: murine leukemia virus (MLV), human T-cell leukemia virus (HTLV), mouse mammary tumour virus (MMTV), Rous sarcoma virus (RSV), Fujinami sarcoma virus (FuSV), Moloney murine leukemia virus (Mo MLV), FBR murine osteosarcoma virus (FBR MSV), Moloney murine sarcoma virus (Mo-MSV), Abelson murine leukemia virus (A-MLV), Avian myelocytomatosis virus-29 (MC29) and Avian erythroblastosis virus (AEV). A detailed list of retroviruses may be found in Coffin et al. (1997) "Retroviruses", Cold Spring Harbour Laboratory Press Eds: J M Coffin, S M Hughes, H E Varmus pp 758-763.

Retroviruses may be broadly divided into two categories, namely "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al (1997) ibid.

The basic structure of retroviral and lentiviral genomes shares many common features such as a 5' LTR and a 3' LTR, between or within which are located a packaging signal to enable the genome to be packaged, a primer binding site, integration sites to enable integration into a target cell genome and gag/pol and env genes encoding the packaging components—these are polypeptides required for the assembly of viral particles. Lentiviruses have additional features, such as the rev gene and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration, and transcription. LTRs also serve as enhancer-promoter sequences and can control the expression of the viral genes.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

In a typical retroviral vector of the present invention, at least part of one or more protein coding regions essential for replication may be removed from the virus; for example, gag/pol and env may be absent or not functional. This makes the viral vector replication-defective.

Lentiviruses are part of a larger group of retroviruses. A detailed list of lentiviruses may be found in Coffin et al (1997) "Retroviruses" Cold Spring Harbour Laboratory Press Eds: J M Coffin, S M Hughes, H E Varmus pp 758-763). In brief, lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV), feline immunodeficiency virus (FM, Maedi visna virus (MVV) and bovine immunodeficiency virus (BIV).

The lentivirus family differs from retroviruses in that lentiviruses have the capability to infect both dividing and non-dividing cells (Lewis et al (1992) EMBO J 11(8):3053-3058 and Lewis and Emerman (1994) J Virol 68 (1):510-516). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects or transduces target cells and expresses NOI.

The lentiviral vector may be derived from either a primate lentivirus (e.g. HIV-1) or a non-primate lentivirus (e.g. EIAV).

In general terms, a typical retroviral vector production system involves the separation of the viral genome from the essential viral packaging functions. As illustrated in FIG. 1 these components are normally provided to the production cells on separate DNA expression cassettes (alternatively known as plasmids, expression plasmids, DNA constructs or expression constructs).

The vector genome comprises the NOI. Vector genomes typically require a packaging signal (ψ), the internal expression cassette harbouring the NOI, (optionally) a post-transcriptional element (PRE), the 3'-ppu and a self-inactivating (SIN) LTR. The R-U5 regions are required for correct polyadenylation of both the vector genome RNA and NOI mRNA, as well as the process of reverse transcription. The vector genome may optionally include an open reading frame, as described in WO 2003/064665, which allows for vector production in the absence of rev.

The packaging functions include the gag/pol and env genes. These are required for the production of vector particles by the production cell. Providing these functions in trans to the genome facilitates the production of replication-defective viral vectors.

Production systems for gamma-retroviral vectors are typically 3-component systems requiring genome, gag/pol and env expression constructs. Production systems for HIV-1-based lentiviral vectors may additionally require the accessory gene rev to be provided and for the vector genome to include the rev-responsive element (RRE). EIAV-based lentiviral vectors do not require rev to be provided in trans if an open-reading frame (ORF) is present within the genome (see WO 2003/064665).

Usually both the "external" promoter (which drives the vector genome cassette) and "internal" promoter (which drives the NOI cassette) encoded within the vector genome cassette are strong eukaryotic or virus promoters, as are those driving the other vector system components. Examples of such promoters include CMV, EF1α, PGK, CAG, TK, SV40 and Ubiquitin promoters. Strong 'synthetic' promoters, such as those generated by DNA libraries (e.g. JeT promoter) may also be used to drive transcription. Alternatively, tissue-specific promoters such as rhodopsin (Rho), rhodopsin kinase (RhoK), cone-rod homeobox containing gene (CRX), neural retina-specific leucine zipper protein (NRL), Vitelliform Macular Dystrophy 2 (VMD2), Tyrosine hydroxylase, neuronal-specific neuronal-specific enolase (NSE) promoter, astrocyte-specific glial fibrillary acidic protein (GFAP) promoter, human α1-antitrypsin (hAAT) promoter, phosphoenolpyruvate carboxykinase (PEPCK), liver fatty acid binding protein promoter, Flt-1 promoter, INF-β promoter, Mb promoter, SP-B promoter, SYN1 promoter, WASP promoter, SV40/hAlb promoter, SV40/CD43, SV40/CD45, NSE/RU5' promoter, ICAM-2 promoter, GPIIb promoter, GFAP promoter, Fibronectin promoter, Endoglin promoter, Elastase-1 promoter, Desmin promoter, CD68 promoter, CD14 promoter and B29 promoter may be used to drive transcription.

Production of retroviral vectors involves either the transient co-transfection of the production cells with these DNA components or use of stable production cell lines wherein all the components are stably integrated within the production cell genome (e.g. Stewart H J, Fong-Wong L, Strickland I, Chipchase D, Kelleher M, Stevenson L, Thoree V, McCarthy J, Ralph G S, Mitrophanous K A and Radcliffe P A. (2011). *Hum Gene Ther*. March; 22 (3):357-69). An alternative approach is to use a stable packaging cell (into which the packaging components are stably integrated) and then transiently transfect in the vector genome plasmid as required (e.g. Stewart, H. J., M. A. Leroux-Carlucci, C. J. Sion, K. A. Mitrophanous and P. A. Radcliffe (2009). *Gene Ther*. June; 16 (6):805-14). It is also feasible that alternative, not complete, packaging cell lines could be generated (just one or two packaging components are stably integrated into the cell lines) and to generate vector the missing components are transiently transfected. The production cell may also express regulatory proteins such as a member of the tet repressor (TetR) protein group of transcription regulators (e.g.T-Rex, Tet-On, and Tet-Off), a member of the cumate inducible switch system group of transcription regulators (e.g. cumate repressor (CymR) protein), or an RNA-binding protein (e.g. TRAP—tryptophan-activated RNA-binding protein).

In one embodiment of the present invention, the viral vector is derived from EIAV. EIAV has the simplest genomic structure of the lentiviruses and is particularly preferred for use in the present invention. In addition to the gag/pol and env genes, EIAV encodes three other genes: tat, rev, and S2. Tat acts as a transcriptional activator of the viral LTR (Derse and Newbold (1993) Virology 194(2):530-536 and Maury et al (1994) Virology 200(2):632-642) and rev regulates and coordinates the expression of viral genes through rev-response elements (RRE) (Martarano et al. (1994) J Virol 68(5):3102-3111). The mechanisms of action of these two proteins are thought to be broadly similar to the analogous mechanisms in the primate viruses (Martarano et al. (1994) J Virol 68(5):3102-3111). The function of S2 is unknown. In addition, an EIAV protein, Ttm, has been identified that is encoded by the first exon of tat spliced to the env coding sequence at the start of the transmembrane protein. In an alternative embodiment of the present invention the viral vector is derived from HIV: HIV differs from EIAV in that it does not encode S2 but unlike EIAV it encodes vif, vpr, vpu and nef.

The term "recombinant retroviral or lentiviral vector" (RRV) refers to a vector with sufficient retroviral genetic information to allow packaging of an RNA genome, in the presence of packaging components, into a viral particle capable of transducing a target cell. Transduction of the target cell may include reverse transcription and integration into the target cell genome. The RRV carries non-viral coding sequences which are to be delivered by the vector to the target cell. A RRV is incapable of independent replication to produce infectious retroviral particles within the target cell. Usually the RRV lacks a functional gag/pol and/or env gene, and/or other genes essential for replication.

Preferably the RRV vector of the present invention has a minimal viral genome.

As used herein, the term "minimal viral genome" means that the viral vector has been manipulated so as to remove the non-essential elements whilst retaining the elements essential to provide the required functionality to infect, transduce and deliver a NOI to a target cell. Further details of this strategy can be found in WO 1998/17815 and WO 99/32646. A minimal EIAV vector lacks tat, rev and S2 genes and neither are these genes provided in trans in the production system. A minimal HIV vector lacks vif, vpr, vpu, tat and nef (FIG. 1).

The expression plasmid used to produce the vector genome within a production cell may include transcriptional regulatory control sequences operably linked to the retroviral genome to direct transcription of the genome in a production cell/packaging cell. These regulatory sequences may be the natural sequences associated with the transcribed retroviral sequence, i.e. the 5' U3 region, or they may be a heterologous promoter such as another viral promoter, for example the CMV promoter, as discussed below. Some lentiviral vector genomes require additional sequences for efficient virus production. For example, particularly in the case of HIV, RRE sequences may be included. However, the requirement for RRE (and dependence on rev which is provided in trans) may be reduced or eliminated by codon optimisation. Further details of this strategy can be found in WO 2001/79518.

Alternative sequences which perform the same function as the rev/RRE system are also known. For example, a functional analogue of the rev/RRE system is found in the Mason Pfizer monkey virus. This is known as the constitutive transport element (CTE) and comprises an RRE-type sequence in the genome which is believed to interact with a factor in the infected cell. The cellular factor can be thought of as a rev analogue. Thus, CTE may be used as an alternative to the rev/RRE system. Any other functional equivalents of the Rev protein which are known or become available may be relevant to the invention. For example, it is also known that the Rex protein of HTLV-I can functionally replace the Rev protein of HIV-1. Rev and RRE may be absent or non-functional in the vector for use in the methods of the present invention; in the alternative rev and RRE, or functionally equivalent system, may be present.

As used herein, the term "functional substitute" means a protein or sequence having an alternative sequence which performs the same function as another protein or sequence. The term "functional substitute" is used interchangeably with "functional equivalent" and "functional analogue" herein with the same meaning.

SIN Vectors

The retroviral vectors of the invention may be used in a self-inactivating (SIN) configuration in which the viral enhancer and promoter sequences have been deleted. SIN vectors can be generated and transduce non-dividing target cells in vivo, ex vivo or in vitro with an efficacy similar to that of non-SIN vectors. The transcriptional inactivation of the long terminal repeat (LTR) in the SIN provirus should prevent mobilisation by replication-competent virus. This should also enable the regulated expression of genes from internal promoters by eliminating any cis-acting effects of the LTR.

By way of example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus. However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it is important to prevent the adventitious activation of any endogenous oncogene. Yu et al., (1986) PNAS 83: 3194-98; Marty et al., (1990) Biochimie 72: 885-7; Naviaux et al., (1996) J. Virol. 70: 5701-5; Iwakuma et al., (1999) Virol. 261: 120-32; Deglon et al., (2000) Human Gene Therapy 11: 179-90. SIN lentiviral vectors are described in U.S. Pat. Nos. 6,924,123 and 7,056,699.

Replication-Defective Lentiviral Vectors

In the genome of a replication-defective lentiviral vector the sequences of gag/pol and/or env may be mutated and/or not functional.

In a typical lentiviral vector of the present invention, at least part of one or more coding regions for proteins essential for virus replication may be removed from the vector. This makes the viral vector replication-defective. Portions of the viral genome may also be replaced by a NOI in order to generate a vector comprising an NOI which is capable of transducing a non-dividing target cell and/or integrating its genome into the target cell genome.

In one embodiment the lentiviral vectors are non-integrating vectors as described in WO 2006/010834 and WO 2007/071994.

In a further embodiment the vectors have the ability to deliver a sequence which is devoid of or lacking viral RNA. In a further embodiment a heterologous binding domain (heterologous to gag) located on the RNA to be delivered and a cognate binding domain on Gag or GagPol can be used to ensure packaging of the RNA to be delivered. Both of these vectors are described in WO 2007/072056.

NOI and Polynucleotides

Polynucleotides of the invention may comprise DNA or RNA. They may be single-stranded or double-stranded. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

The polynucleotides may be modified by any method available in the art. Such modifications may be carried out in order to enhance the in vivo activity or lifespan of the polynucleotides of the invention.

Polynucleotides such as DNA polynucleotides may be produced recombinantly, synthetically or by any means available to those of skill in the art. They may also be cloned by standard techniques.

Longer polynucleotides will generally be produced using recombinant means, for example using polymerase chain reaction (PCR) cloning techniques. This will involve making a pair of primers (e.g. of about 15 to 30 nucleotides) flanking the target sequence which it is desired to clone, bringing the primers into contact with mRNA or cDNA obtained from an animal or human cell, performing PCR under conditions which bring about amplification of the desired region, isolating the amplified fragment (e.g. by purifying the reaction mixture with an agarose gel) and recovering the amplified DNA. The primers may be designed to contain suitable restriction enzyme recognition sites so that the amplified DNA can be cloned into a suitable vector.

Proteins

As used herein, the term "protein" includes single-chain polypeptide molecules as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds.

Variants, Derivatives, Analogues, Homologues and Fragments

In addition to the specific proteins and nucleotides mentioned herein, the present invention also encompasses the use of variants, derivatives, analogues, homologues and fragments thereof.

In the context of the present invention, a variant of any given sequence is a sequence in which the specific sequence of residues (whether amino acid or nucleic acid residues) has been modified in such a manner that the polypeptide or polynucleotide in question retains at least one of its endogenous functions. A variant sequence can be obtained by addition, deletion, substitution, modification, replacement and/or variation of at least one residue present in the naturally-occurring protein.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence retains the required activity or ability. Amino acid substitutions may include the use of non-naturally occurring analogues.

Proteins used in the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R H |
| AROMATIC | | F W Y |

The term "homologue" means an entity having a certain homology with the wild type amino acid sequence and the wild type nucleotide sequence. The term "homology" can be equated with "identity".

In the present context, a homologous sequence is taken to include an amino acid sequence which may be at least 50%, 55%, 65%, 75%, 85% or 90% identical, preferably at least 95%, 97 or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 50%, 55%, 65%, 75%, 85% or 90% identical, preferably at least 95%, 97% or 99% identical to the subject sequence. Although homology can also be considered in terms of similarity, in the context of the present invention it is preferred to express homology in terms of sequence identity.

Homology comparisons can be conducted by eye, or more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package, the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Research 12:387). Examples of other software that can perform sequence comparisons include, but are not limited to, the BLAST package (see Ausubel et al. (1999) ibid-Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol Lett (1999) 174(2):247-50; FEMS Microbiol Lett (1999) 177(1):187-8).

Although the final percentage homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate percentage homology, preferably percentage sequence identity. The software usually does this as part of the sequence comparison and generates a numerical result.

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the break. The DNA is then expressed in accordance with the invention to make the encoded protein. These methods are only illustrative of the numerous standard techniques known in the art for manipulation of DNA sequences and other known techniques may also be used.

All variants, fragments or homologues of the regulatory protein suitable for use in the cells and/or modular constructs of the invention will retain the ability to bind the cognate binding site of the NOI such that translation of the NOI is repressed or prevented in a viral vector production cell.

All variants fragments or homologues of the binding site will retain the ability to bind the cognate RNA-binding protein, such that translation of the NOI is repressed or prevented in a viral vector production cell.

Codon Optimisation

The polynucleotides used in the present invention (including the NOI and/or components of the vector production system) may be codon-optimised. Codon optimisation has previously been described in WO 1999/41397 and WO 2001/79518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including retroviruses, use a large number of rare codons and changing these to correspond to commonly used mammalian codons, increases expression of a gene of interest, e.g. a NOI or packaging components in mammalian production cells, can be achieved. Codon usage tables are known in the art for mammalian cells, as well as for a variety of other organisms.

Codon optimisation of viral vector components has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. In lentiviral vectors codon optimisation also overcomes the Rev/RRE requirement for export, rendering optimised sequences Rev-independent. Codon optimisation also reduces homologous recombination between different constructs within the vector system (for example between the regions of overlap in the gag-pol and env open reading frames). The overall effect of codon optimisation is therefore a notable increase in viral titre and improved safety.

In one embodiment, only codons relating to INS are codon optimised. However, in a much more preferred and practical embodiment, the sequences are codon optimised in their entirety, with some exceptions, for example the sequence encompassing the frameshift site of gag-pol (see below).

The gag-pol gene of lentiviral vectors comprises two overlapping reading frames encoding the gag-pol proteins. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the Gag-Pol proteins. For EIAV the beginning of the overlap has been taken to be nt 1262 (where nucleotide 1 is the A of the gag ATG) and the end of the overlap to be nt 1461. In order to ensure that the frameshift site and the gag-pol overlap are preserved, the wild type sequence has been retained from nt 1156 to 1465.

Derivations from optimal codon usage may be made, for example, in order to accommodate convenient restriction sites, and conservative amino acid changes may be introduced into the Gag-Pol proteins.

In one embodiment, codon optimisation is based on lightly expressed mammalian genes. The third and sometimes the second and third base may be changed.

Due to the degenerate nature of the genetic code, it will be appreciated that numerous gag-pol sequences can be achieved by a skilled worker. Also, there are many retroviral variants described which can be used as a starting point for generating a codon-optimised gag-pol sequence. Lentiviral genomes can be quite variable. For example, there are many quasi-species of HIV-1 which are still functional. This is also the case for EIAV. These variants may be used to enhance particular parts of the transduction process. Examples of HIV-1 variants may be found at the HIV Databases operated by Los Alamos National Security, LLC at http://hiv-web.lanl.gov. Details of EIAV clones may be found at the National Center for Biotechnology Information (NCBI) database located at http://www.ncbi.nlm.nih.gov.

The strategy for codon-optimised gag-pol sequences can be used in relation to any retrovirus. This would apply to all lentiviruses, including EIAV, FIV, BIV, CAEV, VMR, SIV, HIV-1 and HIV-2. In addition, this method could be used to increase expression of genes from HTLV-1, HTLV-2, HFV, HSRV and human endogenous retroviruses (HERV), MLV and other retroviruses.

Codon optimisation can render gag-pol expression Rev-independent. In order to enable the use of anti-rev or RRE factors in the lentiviral vector, however, it would be necessary to render the viral vector generation system totally Rev/RRE-independent. Thus, the genome also needs to be modified. This is achieved by optimising vector genome components.

Advantageously, these modifications also lead to the production of a safer system absent of all additional proteins both in the producer and in the transduced cell.

Common Retroviral Vector Elements

Promoters and Enhancers

Expression of a NOI and polynucleotide may be controlled using control sequences for example transcription regulation elements or translation repression elements, which include promoters, enhancers and other expression regulation signals (e.g. tet repressor (TetR) system) or the Transgene Repression In vector Production cell system (TRIP) or other regulators of NOIs described herein.

Prokaryotic promoters and promoters functional in eukaryotic cells may be used. Tissue-specific or stimuli-specific promoters may be used. Chimeric promoters may also be used comprising sequence elements from two or more different promoters.

Suitable promoting sequences are strong promoters including those derived from the genomes of viruses, such as polyoma virus, adenovirus, fowlpox virus, bovine papilloma virus, avian sarcoma virus, cytomegalovirus (CMV), retrovirus and Simian Virus 40 (SV40), or from heterologous mammalian promoters, such as the actin promoter, EF1α, CAG, TK, SV40, ubiquitin, PGK or ribosomal protein promoter. Alternatively, tissue-specific promoters such as rhodopsin (Rho), rhodopsin kinase (RhoK), cone-rod homeobox containing gene (CRX), neural retina-specific leucine zipper protein (NRL), Vitelliform Macular Dystrophy 2 (VMD2), Tyrosine hydroxylase, neuronal-specific neuronal-specific enolase (NSE) promoter, astrocyte-specific glial fibrillary acidic protein (GFAP) promoter, human α1-antitrypsin (hAAT) promoter, phosphoenolpyruvate carboxykinase (PEPCK), liver fatty acid binding protein promoter, Flt-1 promoter, INF-β promoter, Mb promoter, SP-B promoter, SYN1 promoter, WASP promoter, SV40/hAlb promoter, SV40/CD43, SV40/CD45, NSE/RU5' promoter, ICAM-2 promoter, GPIIb promoter, GFAP promoter, Fibronectin promoter, Endoglin promoter, Elastase-1 promoter, Desmin promoter, CD68 promoter, CD14 promoter and B29 promoter may be used to drive transcription.

Transcription of a NOI may be increased further by inserting an enhancer sequence into the vector. Enhancers are relatively orientation- and position-independent; however, one may employ an enhancer from a eukaryotic cell virus, such as the SV40 enhancer and the CMV early promoter enhancer. The enhancer may be spliced into the vector at a position 5' or 3' to the promoter, but is preferably located at a site 5' from the promoter.

The promoter can additionally include features to ensure or to increase expression in a suitable target cell. For example, the features can be conserved regions e.g. a Pribnow Box or a TATA box. The promoter may contain other sequences to affect (such as to maintain, enhance or decrease) the levels of expression of a nucleotide sequence. Suitable other sequences include the Sh1-intron or an ADH intron. Other sequences include inducible elements, such as temperature, chemical, light or stress inducible elements. Also, suitable elements to enhance transcription or translation may be present.

Regulators of NOIs

A complicating factor in the generation of retroviral packaging/producer cell lines and retroviral vector production is that constitutive expression of certain retroviral vector components and NOIs are cytotoxic leading to death of cells expressing these components and therefore inability to produce vector. Therefore, the expression of these components (e.g. gag-pol and envelope proteins such as VSV-G) must be regulated. The expression of other non-cytotoxic vector components can also be regulated to minimise the metabolic burden on the cell. The modular constructs and/or cells of the invention may comprise cytotoxic and/or non-cytotoxic vector components associated with at least one regulatory element. As used herein, the term "regulatory element" refers to any element capable of affecting, either increasing or decreasing, the expression of an associated gene or protein. A regulatory element includes a gene switch system, transcription regulation element and translation repression element.

A number of prokaryotic regulator systems have been adapted to generate gene switches in mammalian cells. Many retroviral packaging and producer cell lines have been controlled using gene switch systems (e.g. tetracycline and cumate inducible switch systems) thus enabling expression of one or more of the retroviral vector components to be switched on at the time of vector production. Gene switch systems include those of the (TetR) protein group of transcription regulators (e.g.T-Rex, Tet-On, and Tet-Off), those of the cumate inducible switch system group of transcription regulators (e.g. CymR protein) and those involving an RNA-binding protein (e.g. TRAP).

One such tetracycline-inducible system is the tetracycline repressor (TetR) system based on the T-REx™ system. By way of example, in such a system tetracycline operators (TetO$_2$) are placed in a position such that the first nucleotide is 10 bp from the 3' end of the last nucleotide of the TATATAA element of the human cytomegalovirus major immediate early promoter (hCMVp) then TetR alone is capable of acting as a repressor (Yao F, Svensjo T, Winkler T, Lu M, Eriksson C, Eriksson E. Tetracycline repressor, tetR, rather than the tetR-mammalian cell transcription factor fusion derivatives, regulates inducible gene expression in mammalian cells. 1998. *Hum Gene Ther;* 9: 1939-1950). In such a system the expression of the NOI can be controlled by a CMV promoter into which two copies of the TetO$_2$ sequence have been inserted in tandem. TetR homodimers, in the absence of an inducing agent (tetracycline or its analogue doxycycline [dox]), bind to the TetO$_2$ sequences and physically block transcription from the upstream CMV promoter. When present, the inducing agent binds to the TetR homodimers, causing allosteric changes such that it can no longer bind to the TetO$_2$ sequences, resulting in gene expression. The TetR gene used in the Examples disclosed herein has been codon optimised as this was found to improve translation efficiency resulting in tighter control of TetO$_2$ controlled gene expression.

The TRiP system is described in WO 2015/092440 and provides another way of repressing expression of the NOI in the production cells during vector production. The TRAP-binding sequence (e.g. TRAP-tbs) interaction forms the basis for a transgene protein repression system for the production of retroviral vectors, when a constitutive and/or strong promoter, including a tissue-specific promoter, driving the transgene is desirable and particularly when expression of the transgene protein in production cells leads to reduction in vector titres and/or elicits an immune response in vivo due to viral vector delivery of transgene-derived protein (Maunder et al, Nat Commun. (2017) March 27; 8).

Briefly, the TRAP-tbs interaction forms a translational block, repressing translation of the transgene protein (Maunder et al, Nat Commun. (2017) March 27; 8). The translational block is only effective in production cells and as such does not impede the DNA- or RNA-based vector systems. The TRiP system is able to repress translation when the transgene protein is expressed from a constitutive and/or strong promoter, including a tissue-specific promoter from single- or multi cistronic mRNA. It has been demonstrated that unregulated expression of transgene protein can reduce vector titres and affect vector product quality. Repression of transgene protein for both transient and stable PaCL/PCL vector production systems is beneficial for production cells to prevent a reduction in vector titres: where toxicity or molecular burden issues may lead to cellular stress; where transgene protein elicits an immune response in vivo due to viral vector delivery of transgene-derived protein; where the use of gene-editing transgenes may result in on/off target affects; where the transgene protein may affect vector and/or envelope glycoprotein exclusion.

Envelope and Pseudotyping

In one preferred aspect, the retroviral vector of the present invention has been pseudotyped. In this regard, pseudotyping can confer one or more advantages. For example, the env gene product of the HIV based vectors would restrict these vectors to infecting only cells that express a protein called CD4. But if the env gene in these vectors has been substituted with env sequences from other enveloped viruses, then they may have a broader infectious spectrum (Verma and Somia (1997) Nature 389(6648):239-242). By way of example, workers have pseudotyped an HIV based vector with the glycoprotein from VSV (Verma and Somia (1997) Nature 389(6648):239-242).

In another alternative, the Env protein may be a modified Env protein such as a mutant or engineered Env protein. Modifications may be made or selected to introduce targeting ability or to reduce toxicity or for another purpose (Valsesia-Wittman et al 1996 J Virol 70: 2056-64; Nilson et al (1996) Gene Ther 3(4):280-286; and Fielding et al (1998) Blood 91(5):1802-1809 and references cited therein).

The vector may be pseudotyped with any molecule of choice.

As used herein, "env" shall mean an endogenous lentiviral envelope or a heterologous envelope, as described herein.

VSV-G

The envelope glycoprotein (G) of Vesicular stomatitis virus (VSV), a rhabdovirus, is an envelope protein that has been shown to be capable of pseudotyping certain enveloped viruses and viral vector virions.

Its ability to pseudotype MoMLV-based retroviral vectors in the absence of any retroviral envelope proteins was first shown by Emi et al. (1991) Journal of Virology 65:1202-1207). WO 1994/294440 teaches that retroviral vectors may be successfully pseudotyped with VSV-G. These pseudotyped VSV-G vectors may be used to transduce a wide range of mammalian cells. More recently, Abe et al. (1998) J Virol 72(8) 6356-6361 teach that non-infectious retroviral particles can be made infectious by the addition of VSV-G.

Burns et al. (1993) Proc. Natl. Acad. Sci. USA 90:8033-7) successfully pseudotyped the retrovirus MLV with VSV-G and this resulted in a vector having an altered host range compared to MLV in its native form. VSV-G pseudotyped vectors have been shown to infect not only mammalian cells, but also cell lines derived from fish, reptiles and insects (Burns et al. (1993) ibid). They have also been shown to be more efficient than traditional amphotropic envelopes for a variety of cell lines (Yee et al., (1994) Proc. Natl. Acad. Sci. USA 91:9564-9568, Emi et al. (1991) Journal of Virology 65:1202-1207). VSV-G protein can be used to pseudotype certain retroviruses because its cytoplasmic tail is capable of interacting with the retroviral cores.

The provision of a non-retroviral pseudotyping envelope such as VSV-G protein gives the advantage that vector particles can be concentrated to a high titre without loss of infectivity (Akkina et al. (1996) J. Virol. 70:2581-5). Retrovirus envelope proteins are apparently unable to withstand the shearing forces during ultracentrifugation, probably because they consist of two non-covalently linked subunits. The interaction between the subunits may be disrupted by the centrifugation. In comparison the VSV glycoprotein is composed of a single unit. VSV-G protein pseudotyping can therefore offer potential advantages for both efficient target cell infection/transduction and during manufacturing processes.

WO 2000/52188 describes the generation of pseudotyped retroviral vectors, from stable producer cell lines, having vesicular stomatitis virus-G protein (VSV-G) as the membrane-associated viral envelope protein, and provides a gene sequence for the VSV-G protein.

Ross River Virus

The Ross River viral envelope has been used to pseudotype a non-primate lentiviral vector (FIV) and following systemic administration predominantly transduced the liver (Kang et al (2002) J Virol 76(18):9378-9388). Efficiency was reported to be 20-fold greater than obtained with VSV-G pseudotyped vector, and caused less cytotoxicity as measured by serum levels of liver enzymes suggestive of hepatotoxicity.

Baculovirus GP64

The baculovirus GP64 protein has been shown to be an alternative to VSV-G for viral vectors used in the large-scale production of high-titre virus required for clinical and commercial applications (Kumar M, Bradow B P, Zimmerberg J (2003) Hum Gene Ther. 14(1):67-77). Compared with VSV-G-pseudotyped vectors, GP64-pseudotyped vectors have a similar broad tropism and similar native titres. Because, GP64 expression does not kill cells, HEK293T-based cell lines constitutively expressing GP64 can be generated.

Alternative Envelopes

Other envelopes which give reasonable titre when used to pseudotype EIAV include Mokola, Rabies, Ebola and LCMV (lymphocytic choriomeningitis virus). Intravenous infusion into mice of lentivirus pseudotyped with 4070A led to maximal gene expression in the liver.

Packaging Sequence

As utilized within the context of the present invention the term "packaging signal", which is referred to interchangeably as "packaging sequence" or "psi", is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon. In EIAV the packaging signal comprises the R region into the 5' coding region of Gag.

As used herein, the term "extended packaging signal" or "extended packaging sequence" refers to the use of sequences around the psi sequence with further extension into the gag gene. The inclusion of these additional packaging sequences may increase the efficiency of insertion of vector RNA into viral particles.

Feline immunodeficiency virus (FIV) RNA encapsidation determinants have been shown to be discrete and non-continuous, comprising one region at the 5' end of the genomic mRNA (R-U5) and another region that mapped within the proximal 311 nt of gag (Kaye et al., J Virol. October; 69(10):6588-92 (1995).

Internal Ribosome Entry Site (IRES)

Insertion of IRES elements allows expression of multiple coding regions from a single promoter (Adam et al (as above); Koo et al (1992) Virology 186:669-675; Chen et al 1993 J. Virol 67:2142-2148). IRES elements were first found in the non-translated 5' ends of picornaviruses where they promote cap-independent translation of viral proteins (Jang et al (1990) Enzyme 44: 292-309). When located between open reading frames in an RNA, IRES elements allow efficient translation of the downstream open reading frame by promoting entry of the ribosome at the IRES element followed by downstream initiation of translation.

A review on IRES is presented by Mountford and Smith (TIG May 1995 vol 11, No 5:179-184). A number of different IRES sequences are known including those from encephalomyocarditis virus (EMCV) (Ghattas, I. R., et al., Mol. Cell. Biol., 11:5848-5859 (1991); BiP protein [Macejak and Sarnow, Nature 353:91 (1991)]; the Antennapedia gene of Drosophila (exons d and e) [Oh, et al., Genes & Development, 6:1643-1653 (1992)] as well as those in polio virus (PV) [Pelletier and Sonenberg, Nature 334: 320-325 (1988); see also Mountford and Smith, TIG 11, 179-184 (1985)].

IRES elements from PV, EMCV and swine vesicular disease virus have previously been used in retroviral vectors (Coffin et al, as above).

The term "IRES" includes any sequence or combination of sequences which work as or improve the function of an IRES. The IRES(s) may be of viral origin (such as EMCV IRES, PV IRES, or FMDV 2A-like sequences) or cellular origin (such as FGF2 IRES, NRF IRES, Notch 2 IRES or EIF4 IRES).

In order for the IRES to be capable of initiating translation of each polynucleotide it should be located between or prior to the polynucleotides in the modular construct.

The modular constructs utilised for development of stable cell lines require the addition of selectable markers for selection of cells where stable integration has occurred. These selectable markers can be expressed as a single transcription unit within the modular construct or it may be preferable to use IRES elements to initiate translation of the selectable marker in a polycistronic message (Adam et al 1991 J.Virol. 65, 4985). In this invention a number of the modular constructs were designed such that the selectable maker was placed downstream of one of the retroviral vector components utilising an IRES element.

Genetic Orientation and Insulators

It is well known that nucleic acids are directional and this ultimately affects mechanisms such as transcription and replication in the cell. Thus, genes can have relative orientations with respect to one another when part of the same nucleic acid construct.

In certain embodiments of the present invention, the at least two nucleic acid sequences present at the same locus in the cell or construct can be in a reverse and/or alternating orientations. In other words, in certain embodiments of the invention at this particular locus, the pair of sequential genes will not have the same orientation.

The inventors have shown that having the alternating orientations benefits retroviral vector production when the nucleic acids required for vector production are based at the same genetic locus within the host cell, i.e., at the same position on a chromosome. This can help prevent both transcriptional and translational read-through when the region is expressed within the same physical location of the host cell.

This in turn can also improve the safety of the resulting constructs in preventing the generation of replication-competent retroviral vectors.

The inventors have also found that when nucleic acid sequences are in reverse and/or alternating orientations the use of insulators can prevent inappropriate expression or silencing of a NOI from its genetic surroundings.

The term "insulator" refers to a class of DNA sequence elements that when bound to insulator-binding proteins possess an ability to protect genes from surrounding regulator signals. There are two types of insulators: an enhancer blocking function and a chromatin barrier function. When an insulator is situated between a promoter and an enhancer, the enhancer-blocking function of the insulator shields the promoter from the transcription-enhancing influence of the enhancer (Geyer and Corces 1992; Kellum and Schedl 1992). The chromatin barrier insulators function by preventing the advance of nearby condensed chromatin which would lead to a transcriptionally active chromatin region turning into a transcriptionally inactive chromatin region and resulting in silencing of gene expression. Insulators which inhibit the spread of heterochromatin, and thus gene silencing, recruit enzymes involved in histone modifications to prevent this process (Yang J, Corces V G. Chromatin Insulators: A Role in Nuclear Organization and Gene Expression. Advances in cancer research. 2011; 110:43-76. doi:10.1016/B978-0-12-386469-7.00003-7; Huang, Li et al. 2007; Dhillon, Raab et al. 2009). An insulator can have one or both of these functions and the chicken β-globin insulator (cHS4) is one such example. This insulator is the most extensively studied vertebrate insulator, is highly rich in G+C and has both enhancer-blocking and heterochromatic barrier functions (Chung J H, Whitely M, Felsenfeld G. Cell. 1993; 74:505-514). Other such insulators with enhancer blocking functions are not limited to but include the following: human β-globin insulator 5 (HS5), human β-globin insulator 1 (HS1), and chicken β-globin insulator (cHS3) (Farrell CM1, West A G, Felsenfeld G., Mol Cell Biol. 2002 June; 22(11):3820-31; J Ellis et al. EMBO J. 1996 Feb. 1; 15(3): 562-568). In addition to reducing unwanted distal interactions the insulators also help to prevent promoter interference (i.e. where the promoter from one transcription unit impairs expression of an adjacent transcription unit) between adjacent retroviral nucleic acid sequences. If the insulators are used between each of the retroviral vector nucleic acid sequences, then the reduction of direct read-through will help prevent the formation of replication-competent retroviral vector particles.

In one embodiment the insulator is present between each of the retroviral nucleic acid sequences. In one embodiment, the use of insulators prevents promoter-enhancer interactions from one NOI expression cassette interacting with another NOI expression cassette in a modular construct.

In a preferred embodiment an insulator is present between the vector genome and gag-pol sequences. This therefore limits the likelihood of the production of a replication-competent retroviral vector and 'wild-type' like RNA transcripts, improving the safety profile of the construct. The use of insulator elements to improve the expression of stably integrated multigene vectors is cited in Moriarity et al (Modular assembly of transposon integratable multigene vectors using RecWay assembly, Nucleic Acids Res. 2013 April; 41(8):e92).

Vector Titre

The skilled person will understand that there are a number of different methods of determining the titre of retroviral vectors. Titre is often described as transducing units/mL (TU/mL). Titre may be increased by increasing the number of vector particles and by increasing the specific activity of a vector preparation.

Modular Constructs

The present invention also relates to modular nucleic acid constructs (modular constructs). A modular construct is a DNA expression construct comprising two or more nucleic acids used in the production of retroviral vectors. A modular construct can be a DNA plasmid comprising two or more nucleic acids used in the production of retroviral vectors. The nucleic acids can encode for example, gag-pol, rev, env, vector genome. In addition, modular constructs designed for generation of packaging and producer cell lines may additionally need to encode transcriptional regulatory proteins (e.g. TetR, CymR) and/or translational repression proteins (e.g. TRAP) and selectable markers (e.g Zeocin™, hygromycin, blasticidin, puromycin, neomycin resistance genes).

The DNA expression construct can be a DNA plasmid (supercoiled, nicked or linearised), minicircle DNA (linear or supercoiled), plasmid DNA containing just the regions of interest by removal of the plasmid backbone by restriction enzyme digestion and purification, DNA generated using an enzymatic DNA amplification platform e.g. doggybone DNA (dbDNA™) where the final DNA used is in a closed ligated form or where it has been prepared (e.g restriction enzyme digestion) to have open cut ends.

As described herein, current methods for retroviral vector production utilise genetic constructs in which genes essential for retroviral production are introduced into a host cell on separate plasmids by transient transfection methods. This can create batch-to-batch variation and further increases the cost due to the expensive transfection agents and plasmids. By using the modular constructs of the present invention, the number of plasmids which are needed in the transfection process are reduced, thus reducing the burden on labour and material cost.

The use of such modular constructs can also aid in the production of efficient packaging and producer cell lines. In particular, introducing two or more retroviral vector genes onto one modular construct will subsequently reduce the number of stable transfections/transductions, integrations, and selection steps required in order to create the final packaging/producer cell.

In particular, it has been surprising to find that bacterial plasmids are able to perform this function, as it is generally believed that the large genes involved would not permit multiple genes to be stably incorporated into a bacterial plasmid.

In accordance with the present invention, stable cell lines (packaging or producer) for producing the retroviral vectors comprise at least two of the retroviral genes located at the same genetic locus. The table below lists example combinations of nucleic acids which can be located at the same locus in stable vector production cells of the present invention and which are expressed from a single modular construct. The order of each component nucleic acid is also as stated. The asterisk (*) marks combinations which would be suitable for the production of EIAV-based retroviral vectors, as Rev is not an essential component for such vectors. The double asterisk (**) marks combinations which are associated with a regulatory element or are in reverse and/or alternating orientations in the vector.

| Number of expression cassettes | Combination |
|---|---|
| 2 | Genome Rev |
|   | Genome VSV-G* |
|   | Genome Gag-Pol* |
|   | Rev Genome |
|   | Rev VSVG |
|   | Rev Gag-Pol** |
|   | VSVG Genome* |
|   | VSVG Rev |
|   | VSVG Gag-Pol* |
|   | Gag-Pol Genome* |
|   | Gag-Pol Rev** |
|   | Gag-Pol VSVG* |
| 3 | Genome Rev VSVG |
|   | Genome Rev Gag-Pol |
|   | Genome VSVG Rev |
|   | Genome VSVG Gag-Pol* |
|   | Genome Gag-Pol Rev |
|   | Genome Gag-Pol VSVG* |
|   | Rev Genome VSVG |
|   | Rev Genome Gag-Pol |
|   | Rev VSVG Genome |
|   | Rev VSVG Gag-Pol |
|   | Rev Gag-Pol Genome |
|   | Rev Gag-Pol VSVG |
|   | VSVG Genome Rev |
|   | VSVG Genome Gag-Pol* |
|   | VSVG Rev Genome |
|   | VSVG Rev Gag-Pol |
|   | VSVG Gag-Pol Genome* |
|   | VSVG Gag-Pol Rev |
|   | Gag-Pol Genome Rev |
|   | Gag-Pol Genome VSVG* |
|   | Gag-Pol Rev Genome |
|   | Gag-Pol Rev VSVG |
|   | Gag-Pol VSVG Genome* |
|   | Gag-Pol VSVG Rev |
| 4 | Genome Rev VSVG Gag-Pol |
|   | Genome Rev Gag-Pol VSVG |
|   | Genome VSVG Rev Gag-Pol |
|   | Genome VSVG Gag-Pol Rev |
|   | Genome Gag-Pol Rev VSVG |
|   | Genome Gag-Pol VSVG Rev |
|   | Rev Genome VSVG Gag-Pol |
|   | Rev Genome Gag-Pol VSVG |
|   | Rev VSVG Genome Gag-Pol |
|   | Rev VSVG Gag-Pol Genome |
|   | Rev Gag-Pol Genome VSVG |
|   | Rev Gag-Pol VSVG Genome |
|   | VSVG Genome Rev Gag-Pol |
|   | VSVG Genome Gag-Pol Rev |
|   | VSVG Rev Genome Gag-Pol |
|   | VSVG Rev Gag-Pol Genome |
|   | VSVG Gag-Pol Genome Rev |
|   | VSVG Gag-Pol Rev Genome |
|   | Gag-Pol Genome Rev VSVG |
|   | Gag-Pol Genome VSVG Rev |
|   | Gag-Pol Rev Genome VSVG |
|   | Gag-Pol Rev VSVG Genome |
|   | Gag-Pol VSVG Genome Rev |
|   | Gag-Pol VSVG Rev Genome |

In one embodiment of the present invention, the cell or vector of the present invention does not contain an origin of replication sequence derived from a PAC, BAC, YAC, cosmid or fosmid. PAC, BAC, YAC, cosmid and fosmids are artificially generated nucleic acid vectors designed to hold large quantities of DNA. Thus, their core sequences are well known and defined in the art.

Retroviral Vector Production Systems and Cells

An aspect of the invention relates to a retroviral vector production system comprising a set of nucleic acid sequences encoding the components required for production of the retroviral vector.

"Viral vector production system" or "vector production system" or "production system" is to be understood as a system comprising the necessary components for retroviral vector production.

Accordingly, the vector production system comprises a set of nucleic acid sequences which encode the components necessary to generate retroviral vector particles.

In one embodiment of the invention, the viral vector production system comprises nucleic acid sequences encoding Gag and Gag/Pol proteins, and Env protein thereof and the vector genome sequence. The production system may optionally comprise a nucleic acid sequence encoding the Rev protein, or functional substitute thereof.

In an embodiment, the retroviral vector is derived from a lentivirus. In another embodiment, the retroviral vector is derived from HIV-1, HIV-2, SIV, FIV, BIV, EIAV, CAEV or Visna lentivirus. Another aspect of the invention relates to a set of DNA constructs for use in the retroviral vector production system of the invention comprising the modular constructs of the invention. In one embodiment of the invention, the set of DNA constructs additionally comprises a DNA construct encoding Rev protein or a functional substitute thereof.

Another aspect of the invention relates to a retroviral vector production cell comprising the nucleic acid sequence, the viral vector production system, or some or all of the modular constructs of the invention.

A "viral vector production cell", "vector production cell", or "production cell" is to be understood as a cell that is capable of producing a retroviral vector or retroviral vector particle. Retroviral vector production cells may be "producer cells" or "packaging cells". One or more DNA constructs of the viral vector system may be either stably integrated or episomally maintained within the viral vector production cell. Alternatively, all the DNA components of the viral vector system may be transiently transfected into the viral vector production cell. In yet another alternative, a production cell stably expressing some of the components may be transiently transfected with the remaining components required for vector production.

As used herein, the term "packaging cell" refers to a cell which contains the elements necessary for production of retroviral vector particles but which lacks the vector genome. Optionally, such packaging cells contain one or more expression cassettes which are capable of expressing viral structural proteins (such as gag, gag/pol and env).

Producer cells/packaging cells can be of any suitable cell type. Producer cells are generally mammalian cells but can be, for example, insect cells.

As used herein, the term "producer/production cell" or "vector producing/production cell" refers to a cell which contains all the elements necessary for production of retroviral vector particles. The producer cell may be either a stable producer cell line or derived transiently or may be a stable packaging cell wherein the retroviral genome is transiently expressed.

The vector production cells may be cells cultured in vitro such as a tissue culture cell line. Suitable cell lines include, but are not limited to, mammalian cells such as murine fibroblast derived cell lines or human cell lines. Preferably the vector production cells are derived from a human cell line.

Cells and Production Methods

Another aspect of the invention relates to a process for producing retroviral vectors comprising introducing the nucleic acid sequences described herein into a cell (e.g. a host cell) and culturing the cell under conditions suitable for the production of the retroviral vectors.

Therefore, in one aspect the present invention provides a method for generating a production cell for producing retroviral vectors, comprising the steps of:
 a) introducing a modular construct of the invention into a mammalian cell;
 and
 b) optionally selecting for a mammalian cell which has the at least two nucleic acid sequences integrated within its genome.

In a further aspect the present invention provides a method for generating a stable cell for producing retroviral vectors, comprising the steps of:
 a) introducing a modular construct of the invention into a mammalian cell;
 and
 b) selecting for a mammalian cell which has the at least two nucleic acid sequences integrated within its genome.

In a further aspect, the present invention provides a method for generating a transient production cell for producing retroviral vectors, comprising introducing at least one modular construct of the invention into a mammalian cell.

In a further aspect, the present invention provides a method for producing a replication defective retroviral vector, comprising the steps of:
 a) introducing a modular construct of the invention into a mammalian cell;
 b) selecting for a mammalian cell which has the at least two nucleic acid sequences integrated within its genome
 c) optionally introducing a nucleic acid vector which is different to the modular construct into the selected mammalian cell;
 d) further culturing the mammalian cell under conditions in which the replication defective retroviral vector is produced;
 and optionally
 e) isolating the replication defective retroviral vector.

In a further aspect, the present invention provides a method for producing a replication defective retroviral vector, comprising the steps of:
 a) introducing a modular construct of the invention into a mammalian cell;
 b) optionally introducing a nucleic acid vector which is different to the modular construct into the mammalian cell; and
 c) further culturing the mammalian cell under conditions in which the replication defective retroviral vector is produced;
 and optionally d) isolating the replication defective retroviral vector.

In a further aspect, the present invention provides a replication defective retroviral vector produced by any method of the invention.

Suitable production cells are those cells which are capable of producing viral vectors or viral vector particles when cultured under appropriate conditions. They are generally mammalian or human cells, for example HEK293T, HEK293, CAP, CAP-T or CHO cells, but can be, for example, insect cells such as SF9 cells.

Methods for introducing nucleic acids into production cells are well known in the art and have been described previously.

Stable cells may be packaging or producer cells. To generate producer cells from packaging cells the vector genome DNA construct may be introduced stably or transiently. Packaging/producer cells can be generated by transducing a suitable cell line with a retroviral vector which expresses one of the components of the packaging/producer cell, i.e. a genome, the gag-pol components and an envelope as described in WO 2004/022761.

Alternatively, the nucleic acid can be transfected into cells and then integration into the production cell genome occurs infrequently and randomly. The transfection methods may be performed using methods well known in the art. For example, the transfection process may be performed using calcium phosphate or commercially available formulations such as Lipofectamine™ 2000CD (Invitrogen, CA), FuGENE® HD or polyethylenimine (PEI). Alternatively, modular constructs of the invention may be introduced into the production cell via electroporation. The skilled person will be aware of methods to encourage integration of the nucleic acids into production cells. For example, linearising a nucleic acid construct can help if it is naturally circular. Less random integration methodologies may involve the nucleic acid construct comprising of areas of shared homology with the endogenous chromosomes of the mammalian host cell to guide integration to a selected site within the endogenous genome. Furthermore, if recombination sites are present on the construct then these can be used for targeted recombination. For example, the nucleic acid construct may contain a loxP site which allows for targeted integration when combined with Cre recombinase (i.e. using the Cre/lox system derived from P1 bacteriophage). Alternatively or additionally, the recombination site is an att site (e.g. from λ phage), wherein the att site permits site-directed integration in the presence of a lambda integrase. This would allow the retroviral genes to be targeted to a locus within the host cellular genome which allows for high and/or stable expression.

Other methods of targeted integration are well known in the art. For example, methods of inducing targeted cleavage of genomic DNA can be used to encourage targeted recombination at a selected chromosomal locus. These methods often involve the use of methods or systems to induce a double strand break (DSB) e.g. a nick in the endogenous genome to induce repair of the break by physiological mechanisms such as non-homologous end joining (NHEJ). Cleavage can occur through the use of specific nucleases such as engineered zinc finger nucleases (ZFN), transcription-activator like effector nucleases (TALENs), using CRISPR/Cas9 systems with an engineered crRNA/tracr RNA ('single guide RNA') to guide specific cleavage, and/or using nucleases based on the Argonaute system (e.g., from *T. thermophilus*).

Packaging/producer cell lines can be generated by integration of nucleic acids using methods of just retroviral transduction or just nucleic acid transfection, or a combination of both can be used.

Methods for generating retroviral vectors from production cells and in particular the processing of retroviral vectors are described in WO 2009/153563.

In one embodiment, the production cell may comprise the RNA-binding protein (e.g. tryptophan RNA-binding attenuation protein, TRAP) and/or the Tet Repressor (TetR) protein or alternative regulatory proteins (e.g. CymR).

Production of retroviral vector from production cells can be via transfection methods, from production from stable cell lines which can include induction steps (e.g. doxycycline induction) or via a combination of both. The transfection methods may be performed using methods well known in the art, and examples have been described previously.

Production cells, either packaging or producer cell lines or those transiently transfected with the retroviral vector encoding components are cultured to increase cell and virus numbers and/or virus titres. Culturing a cell is performed to enable it to metabolize, and/or grow and/or divide and/or produce viral vectors of interest according to the invention. This can be accomplished by methods well known to persons skilled in the art, and includes but is not limited to providing nutrients for the cell, for instance in the appropriate culture media. The methods may comprise growth adhering to surfaces, growth in suspension, or combinations thereof. Culturing can be done for instance in tissue culture flasks, tissue culture multiwell plates, dishes, roller bottles, wave bags or in bioreactors, using batch, fed-batch, continuous systems and the like. In order to achieve large scale production of viral vector through cell culture it is preferred in the art to have cells capable of growing in suspension. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

Preferably cells are initially 'bulked up' in tissue culture flasks or bioreactors and subsequently grown in multi-layered culture vessels or large bioreactors (greater than 50 L) to generate the vector producing cells of the present invention.

Preferably cells are grown in an adherent mode to generate the vector producing cells of the present invention.

Preferably cells are grown in a suspension mode to generate the vector producing cells of the present invention.

Use

Another aspect of the invention relates to the use of the retroviral vector of the invention or a cell or tissue transduced with the retroviral vector of the invention in medicine.

Another aspect of the invention relates to the use of the retroviral vector of the invention, a production cell of the invention or a cell or tissue transduced with the retroviral vector of the invention for the preparation of a medicament to deliver a nucleotide of interest to a target site in need of the same. Such uses of the retroviral vector or transduced cell of the invention may be for therapeutic or diagnostic purposes, as described previously.

Another aspect of the invention relates to a cell transduced by the retroviral vector of the invention.

A "cell transduced by a viral vector particle" is to be understood as a cell, in particular a target cell, into which the nucleic acid carried by the viral vector particle has been transferred.

Pharmaceutical Compositions

Another aspect of the invention relates to a pharmaceutical composition comprising the retroviral vector of the invention or a cell or tissue transduced with the viral vector of the invention, in combination with a pharmaceutically acceptable carrier, diluent or excipient.

The present invention provides a pharmaceutical composition for treating an individual by gene therapy, wherein the composition comprises a therapeutically effective amount of a retroviral vector. The pharmaceutical composition may be for human or animal usage.

The composition may comprise a pharmaceutically acceptable carrier, diluent, excipient or adjuvant. The choice of pharmaceutical carrier, excipient or diluent can be made with regard to the intended route of administration and standard pharmaceutical practice. The pharmaceutical compositions may comprise, or be in addition to, the carrier, excipient or diluent any suitable binder(s), lubricant(s), suspending agent(s), coating agent(s), solubilising agent(s) and other carrier agents that may aid or increase vector entry into the target site (such as for example a lipid delivery system).

Where appropriate, the composition can be administered by any one or more of inhalation; in the form of a suppository or pessary; topically in the form of a lotion, solution, cream, ointment or dusting powder; by use of a skin patch; orally in the form of tablets containing excipients such as starch or lactose, or in capsules or ovules either alone or in admixture with excipients, or in the form of elixirs, solutions or suspensions containing flavouring or colouring agents; or they can be injected parenterally, for example intracavernosally, intravenously, intramuscularly, intracranially, intraoccularly intraperitoneally, or subcutaneously. For parenteral administration, the compositions may be best used in the form of a sterile aqueous solution which may contain other substances, for example enough salts or monosaccharides to make the solution isotonic with blood. For buccal or sublingual administration, the compositions may be administered in the form of tablets or lozenges which can be formulated in a conventional manner.

The retroviral vector of the invention may also be used to transduce target cells or target tissue ex vivo prior to transfer of said target cell or tissue into a patient in need of the same.

An example of such cell may be autologous T cells and an example of such tissue may be a donor cornea.

Various preferred features and embodiments of the present invention will now be described by way of non-limiting examples.

EXAMPLES

The HEK293T.TetR14 cell used in the studies described in the following examples, constitutively expresses the tetracycline repressor (TetR) protein. As expression of HIV-1 gagpol and VSV-G have been implicated as being toxic to the cells, the expression constructs for these proteins include the hCMV promoter into which two copies of the $TetO_2$ sequence have been inserted in tandem. TetR binds to the $TetO_2$ sequences and prevents transcription from occurring in the HEK293T.TetR14 cells. When expression of the genes is required, they can be induced by the addition of doxycycline or tetracycline to the cells. These inducing agents bind to the TetR homodimers which causes allosteric changes such that it can no longer bind to the $TetO_2$ sequences and gene expression can proceed unhindered.

Example 1

Evaluation of a Full Transient Modular Plasmid

Figure 2:
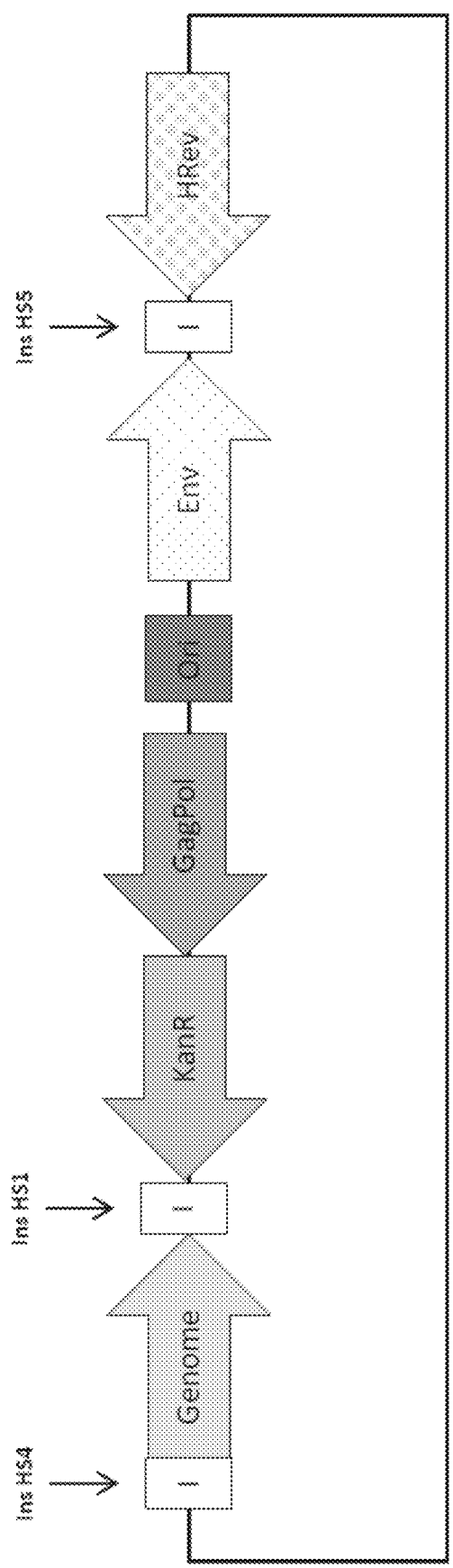
FIG. 2: A schematic of the OXB full transient modular construct (pOXB_Transient_Modular); HS1, HS4 and HS5 are well known insulator sequences
Figure 3:
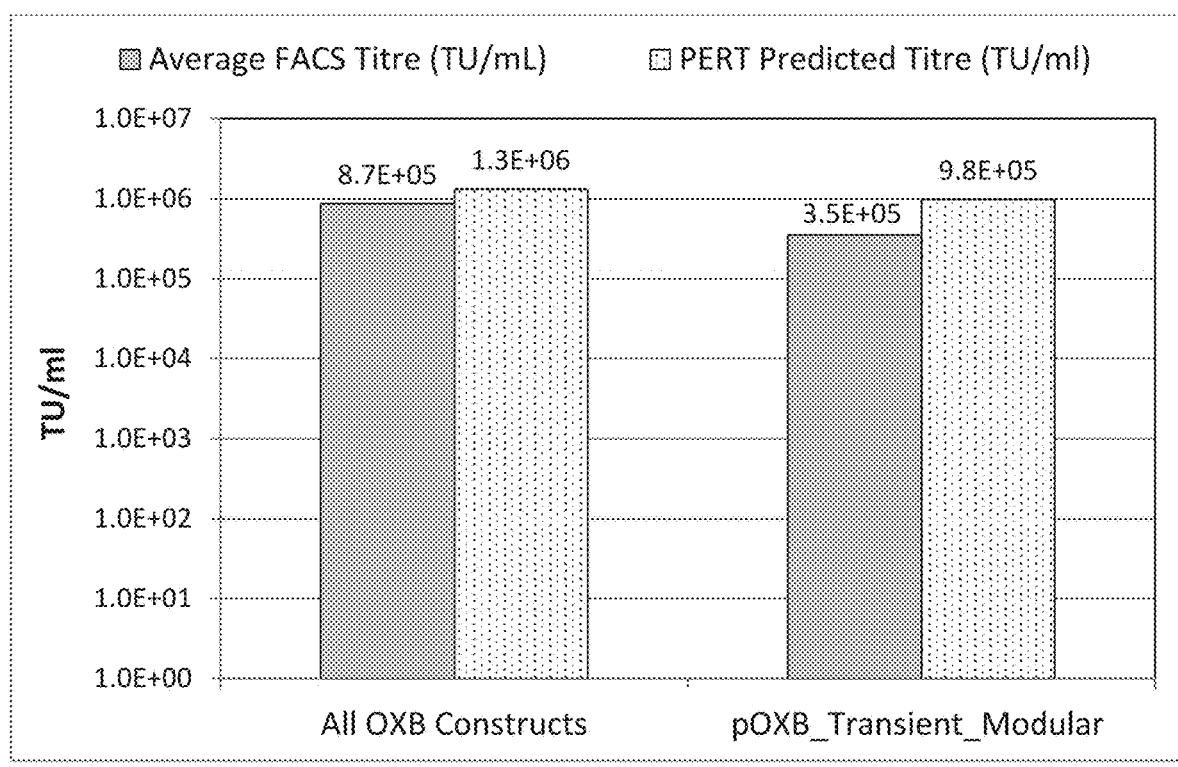
FIG. 3: Biological FACS and PERT predicted titre of LV-GFP vector produced from HEK293T cells that had been transiently transfected with the Transient Modular Construct (pOXB_Transient_Modular) relative to LV-GFP vector produced using the standard transient four plasmid co-transfection process (all OXB constructs separately). Vector production was assessed by GFP FACS titre assay and PERT predicted titre analysis (shown are average titres from harvest 2).

HIV-1-GFP vector was generated in HEK293T.TetR14 cells (constitutively express the TetR protein) using the full modular DNA constructs (pOXB_Transient_Modular) that is shown in FIG. 2, or by the standard transient co-transfection process using an HIV-1 GFP genome plasmid and three inducible packaging component plasmids (FIG. 1). The standard transient co-transfection process generated vector with an average GFP FACS titre of 8.7E+05 TU/ml. When the full transient modular plasmid was used, vector was generated with an average titre of 3.5E+05 TU/ml, which is only 2.5-fold lower than the standard transient co-transfection process (FIG. 3). These results suggest that the vector titres produced using the multicomponent transient transfection system or the transient modular plasmid are surprisingly similar.

Figure 4:
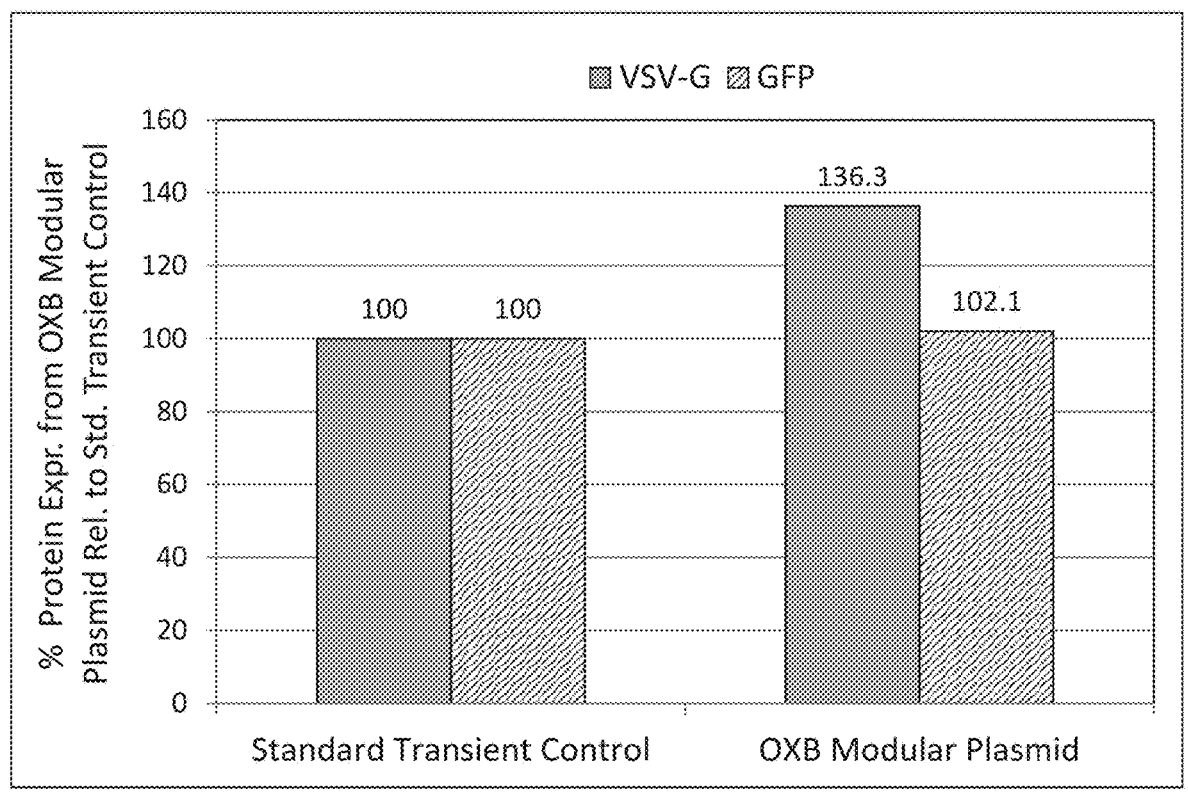
FIG. 4: Percentage VSV-G & GFP Protein Expression from HEK293T Cells Transiently Transfected with the Transient Modular Construct Relative to the Standard Transient Transfection Process. Western blot images were quantified by densitometry and VSV-G and GFP protein expression from the standard transient transfection control were set at 100%. The VSV-G and GFP expression from HEK293T post-production cells transiently transfected with the transient modular construct are expressed as a percentage relative to VSV-G and GFP expression from HEK293T cells transiently transfected with the standard control LV plasmids.

PERT analysis of vector generated from harvest 2 was normalised to the known reference standard titre thereby generating a PERT predicted titre (TU/mL). PERT predicted titres from vector generated using the full modular DNA construct (pOXB_Transient_Modular) demonstrated comparable PERT predicted titres to those obtained from vector generated using the standard transient transfection process (only 1.1-fold lower) (FIG. 3). Further to these experiments, protein analysis by Western blot of the post production cells from both systems revealed consistent results to those attained via both GFP FACS and PERT analysis with a similar level of GFP protein expression being observed and a 36% increase in VSV-G protein expression levels (FIG. 4).

Taken together, these results surprisingly indicated that the pOXB_Transient_Modular construct performs at a similar capacity to when all 4 individual vector component plasmids are co-transfected. As such, the full modular construct could be used to streamline the transient transfection process, reducing plasmid manufacturing costs and possibly reducing the transfection reagent requirements of the system.

Example 2

Evaluation of Lentiviral Vector Production Using Modular Constructs in a Transient Transfection Process Modular constructs shown in FIG. 5 were evaluated by the transient co-transfection system using the modular construct that was under assessment, plus remaining single component plasmids to complete the vector system. All modular constructs tested in this experiment generated vector with GFP FACS titres above 4E+04 TU/ml, confirming that all modular combinations that had been evaluated were capable of producing lentiviral vector using a transient transfection process. The process of generating GFP vector by transient co-transfection of HEK293T cells with a combination of modular constructs and single component plasmids was not optimised and was based on the optimal transient co-transfection process when four individual plasmids are utilised. Therefore, it is likely that with further optimisation the lentiviral vector yields could be improved. Parameters which may be optimised include: seeding densities, modular construct transfection amounts, transfection reagent amounts, harvest timings and induction timings. Only vector from harvest 2 was analysed in this experiment. The results are summarised in FIG. 5.

Example 3

Modular Lentiviral Vector Constructs Evaluated Using the Stable Cell Line Process to Generate Pools of Packaging Cell Lines Stable pools of packaging cell lines were generated by stable transfection using different combinations of single component plasmids or modular lentiviral vector constructs followed by a period of antibiotic selection. Antibiotic selection ensured selection of only those cells where the lentiviral vector packaging components had been integrated into the host cells genomes. Following a period of cell culture, which ensured all un-integrated plasmid DNAs had been diluted out from the cell cultures, resulting pools of packaging cells were tested for their ability to generate lentiviral vectors containing GFP following transient transfection of HIV-1 GFP genome (and Rev for PAC006) and doxycycline induction. FIG. 6 details the modular construct and single plasmid combinations that were used in the generation of each of the pools of packaging cell lines. In addition, FIG. 6 details the resulting GFP FACS titres (TU/ml) of the GFP vector that was produced from each pool of packaging cells following transient transfection of HIV-1 GFP genome (and HIV-1 Rev for PAC006) and doxycycline induction. Surprisingly, the results indicated that all pools of packaging cells generated GFP vector. Furthermore, lentiviral vector titres from all pools of packaging cells (except PAC002) demonstrated titres that were comparable (within 2-fold) to vector produced from a packaging cell line pool generated when individual separate packaging components had been stably integrated (PAC001).

Figure 7:
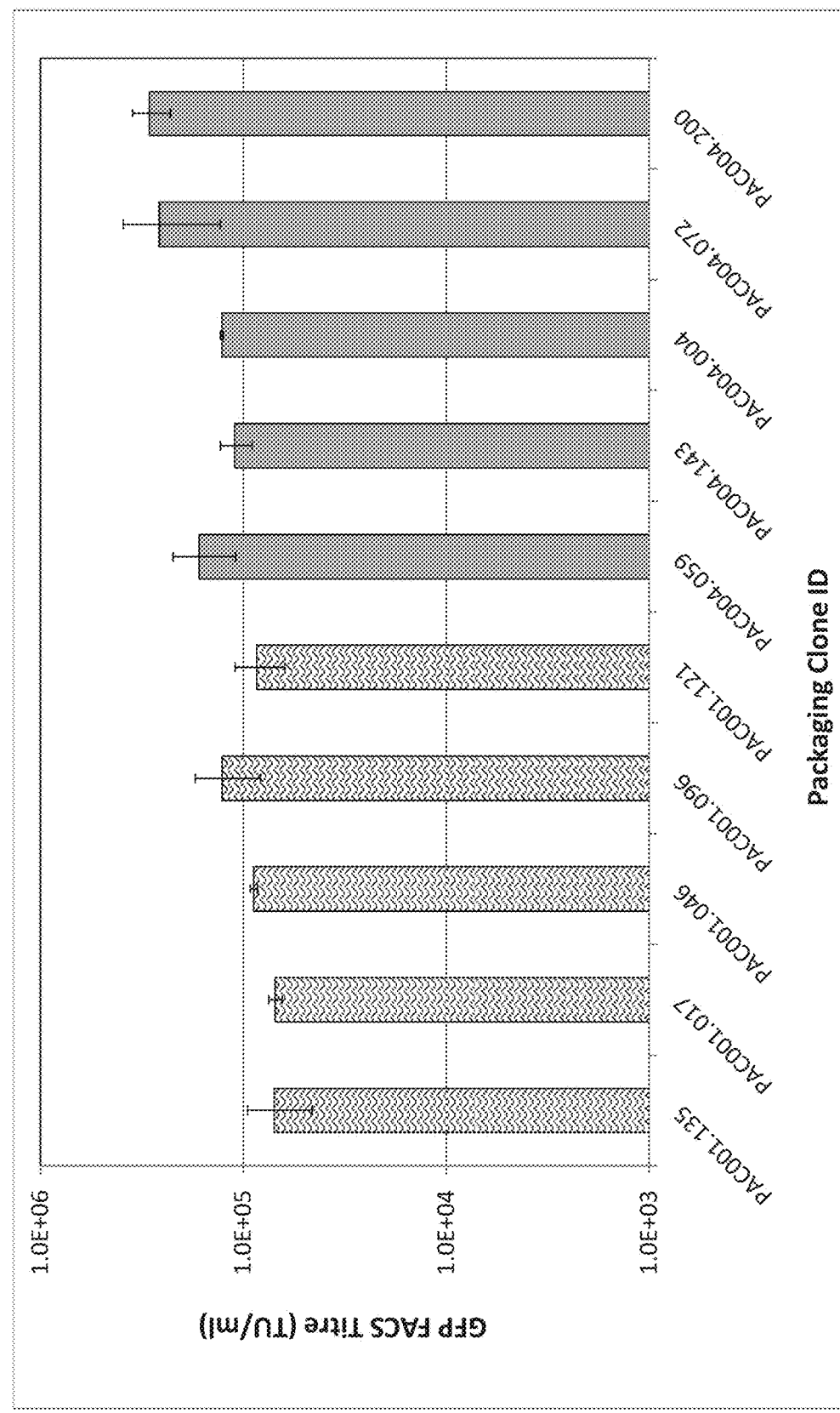
FIG. 7: LV production from the 5 best stable packaging clones generated using either single plasmids (PAC001) or a combination of modular constructs and single plasmids (PAC004: see FIG. 6).

Further to the generation of pools of cells a number of clones were isolated from the packaging cell line strategies PAC001 (single plasmid components) and PAC004 (modular constructs and single plasmid components). The five best clones from each strategy were evaluated for their ability to produce GFP vector following transient transfection of HIV-GFP genome and induction with doxycycline (FIG. 7). Results indicate that the strategy that used a combination of modular constructs and single component plasmids (PAC004, see FIG. 6) led to the generation of packaging clones that on average yielded higher titre GFP vector than achieved from packaging clones isolated from a pool of cells that had been generated using the standard single packaging lentiviral vector plasmids (PAC001, see FIG. 6).

Example 4

Modular Lentiviral Vector Constructs Evaluated Using the Lentiviral Vector Stable Cell Line Process to Generate Producer Cell Lines Stable pools of producer cell lines were generated by stable transfection using different combinations of single component plasmids or modular lentiviral vector constructs followed by a period of antibiotic selection. Following a period of cell culture, which ensured all un-integrated plasmid DNAs had been diluted out from the cell cultures, resulting pools of producer cells were tested for their ability to generate GFP vector following doxycycline induction. FIG. 8 details the modular construct and single plasmid combinations that were used in the generation of each of the pools of producer cell lines. In addition, FIG. 8 details the resulting GFP FACS titres (TU/ml) of the GFP vector that was produced from each pool of producer cells following doxycycline induction. Results demonstrated that all pools of producer cells generated GFP vector with titres that were comparable (within 2-fold) to vector produced from a producer cell line pool generated when individual separate packaging components had been stably integrated (Single component constructs, see FIG. 8).

Example 5

Figure 9:
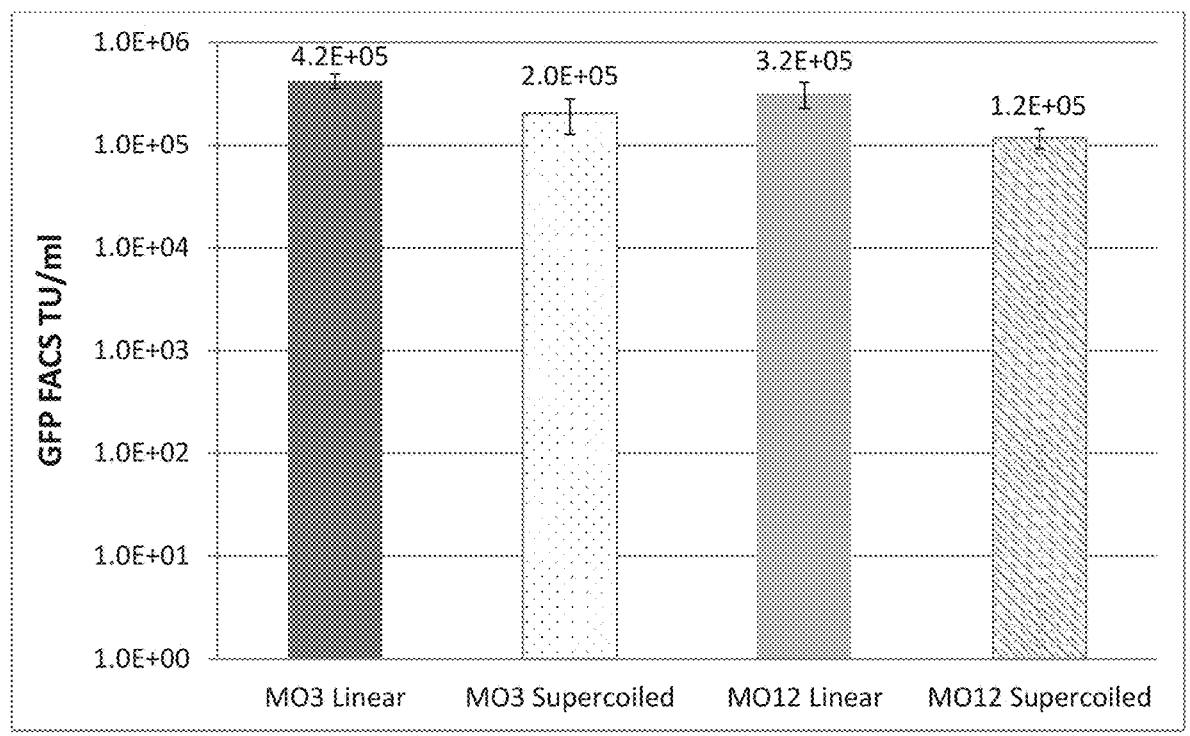
FIG. 9: GFP FACS titre (TU/ml) from HEK293T Cells Stably Transfected with the Modular Constructs in Linear or Supercoiled Form. LV-GFP vector production from stable producer cell lines that were generated by stable transfection using VSV-G-Rev Modular Constructs (MO3 and MO12; see FIG. 8) and single GagPol and genome constructs. The plasmid combinations evaluated were either supercoiled or linearised. Vector was produced and quantified by GFP FACS titre assay.

Retroviral Stable Producer Cell Line Process Evaluated Using Linearised Versus Supercoiled Constructs To investigate whether the generation of stable cell lines would benefit from using linear DNA constructs or supercoiled DNA constructs, stable pools of producer cell lines were generated by stable transfection using VSV-G-Rev Modular Constructs (MO3 and MO12; see FIG. 8) and single GagPol and genome plasmids, in either the linearised or supercoiled formats. Vector production was assessed by GFP FACS titre assay at 6-well scale (FIG. 9). Results indicate that linearisation of the modular constructs prior to stable transfection resulted in a pool of producer cells lines that could produce higher titre lentiviral vectors than when the modular construct was introduced into the cell in the supercoiled form (greater than 2-fold).

Materials and Methods

Plasmids
Plasmids Used for Transient Transfection

The minimal HIV-1 genome plasmid (pRKHVCG) is a SIN vector that contains the GFP gene under the control of an internal human CMV promoter. The VSV-G envelope plasmids are based on the VSV-G plasmid (pHG) that has been previously described (Farley D C et al. (2007). *J Gene Med;* 9: 345-356). HIV-1 GagPol plasmids contain codon optimised. HIV-1 Gag/Pol and are based on the plasmid (pSYNGP) that has been previously described (Kotsopoulou E et al. (2000) *Journal Of Virology;* 74: 4539-4852 and WO 2001/079518) and HIV-1 Rev plasmids were also utilised that, were based on pCMV-Rev (Kotsopoulou E et al. (2000) *Journal Of Virology;* 74: 4539-4852).
Modular Plasmids The modular constructs and single plasmids tested in the Examples herein were constructed based on the plasmids detailed above but additionally include the inducible TetO2 elements and selectable makers for stable cell line development. The only exception to this was the full modular transient construct (pOXB_Transient_Modular) where no TetO2 elements or selectable markers were included. The following table lists the modular constructs which were tested in the Examples herein.

TABLE 1

Modular constructs and Single plasmids used in the Examples herein

| ID | Description | Construct |
|---|---|---|
| pOXB_Transient_Modular | VSV-G + HIV-1 GagPol + HIV-1 Rev + HIV-1 GFP genome | pOXB_Transient_Modular |
| pRKHVCG | HIV-1 SIN genome expressing GFP | Also known as pOXB.HVCG |
| pPCL-HVCG-Hyg | HIV-1 SIN genome expressing GFP | pPCL-HVCG-Hyg |

TABLE 1-continued

Modular constructs and Single plasmids used in the Examples herein

| ID | Description | Construct |
|---|---|---|
| pOXB.TetO2.HSGP.Hyg | HIV-1 inducible GagPol + promoter-HygR | pOXB.TetO2.HSGP.Hyg |
| pOXB.TetO2.HSGP.Bsr | HIV-1 inducible GagPol + promoter-BsrR | pOXB.TetO2.HSGP.Bsr |
| pPC-T-VSVG-Zeo | Inducible VSV-G + promoter-ZeoR | pPC-T-VSVG-Zeo |
| pPC-T-HRev | HIV-1 inducible Rev | pPC-T-HRev |
| MO1 | HIV-1 SIN genome expressing GFP - inducible HIV-1 Rev - promoter - BsrR | pPCL-HVCG-T-HRev-Bsr |
| MO3 | Inducible VSV-G + inducible HIV-1 Rev + promoter-ZeoR | pPC-T-VSVG-T-HRev-Zeo |
| MO4 | HIV-1 inducible GagPol + inducible HIV-1 Rev + promoter- HygroR | pPC-T-GagPol-T-HRev-Hyg |
| MO5 | HIV-1 inducible GagPol + inducible VSV-G + inducible HIV-1 Rev + promoter-ZeoR | pPC-T-GagPol-T-VSVG-T-HRev-Zeo |
| MO6 | HIV-1 genome + HIV-1 inducible GagPol + inducible HIV-1 Rev + inducible VSV-G + promoter- HygroR | pPCL-HVCG-T-GagPol-T-HRev-T-VSVG-Hyg |
| MO11 | HIV-1 genome + HIV-1 Rev (non-inducible) + IRES - BsrR | pPCL-HVCG-HRev-IRES-Bsr |
| MO12 | Inducible VSV-G + HIV-1 Rev (non-inducible) - IRES- ZeoR | pPC-T-VSVG-HRev-IRES-Zeo |
| MO13 | HIV-1 inducible GagPol + HIV-1 Rev (non-inducible) - IRES-HygroR | pPC-T-GagPol-HRev-IRES-Hyg |
| MO14 | HIV-1 inducible GagPol + inducible VSV-G + HIV-1 Rev (non-inducible) - IRES - ZeoR | pPC-T-GagPol-T-VSVG-HRev-IRES-Zeo |
| MO15 | HIV-1 genome + HIV-1 inducible GagPol + inducible VSV-G + HIV-1 Rev (non-inducible) - IRES - ZeoR | pPCL-HVCG-T-GagPol-T-VSVG-HRev-IRES-Zeo |
| MO20 | HIV-1 inducible GagPol + inducible VSV-G + promoter + ZeoR | pPC-T-GagPol-T-VSVG-Zeo |
| MO21 | HIV-1 genome + inducible HIV-1 Rev + promoter-HygroR | pPCL-HVCG-T-HRev-Hyg |

Cell Lines

HEK293I cells used for transient transfection and generation of packaging and producer cell lines were obtained from M. Calos (Stanford University). HEK293I cells were maintained in Dulbecco's modified Eagle's medium (DMEM) (Sigma, Poole, UK, Cat. D5671) containing 10% (v/v) foetal calf serum (FCS) and supplemented with 2 mM L-Glutamine (Sigma, Cat. G7513) and 1% non-essential amino acids (Sigma, M7145).

Stable Cell Lines

HEK293-TetR Cell Line

HEK293T cells stably expressing the codon optimised tetracycline repressor (coTetR) protein were generated by transfecting a 10 cm dish containing 3E+06 HEK293T cells with linearised pPuro-coTetR plasmid DNA using Lipofectamine™ 2000 CD according to the manufacturer's instructions. Media was replaced with conditioned media containing puromycin (0.6 μg/ml) 48 h post-transfection to select transfectants. Two weeks post selection individual clones were isolated from the mixed population by limiting dilution in conditioned media.

Retroviral Vector Packaging Cell Lines

Lentiviral vector (HIV-1 based) packaging cell line pools were generated by transfecting a 10 cm dish containing 3.5E+06 HEK293T-TetR cells with linearised single plasmids and/or modular constructs encoding inducible packaging components (HIV-1 inducible GagPol, HIV-1 inducible Rev and inducible envelope (VSV-G)) using Lipofectamine™ 2000 CD. Forty-eight hours post-transfection the media was replaced with condition media containing the relevant antibiotic(s) (e.g Zeocin™, blasticidin) for selection of cells containing the required integrated nucleic acid sequences. When the packaging cell line pools had recovered from selection, they were cultured for 2 weeks prior to screening for LV productivity.

When individual clonal cell lines were required then clones were isolated by cloning by limiting dilution and screened for LV production before being expanded and screened for LV production at a larger scale.

Retroviral Vector Producer Cell Lines

Lentiviral vector (HIV-1 GFP) producer cell line pools were generated by transfecting 4.0E+06 HEK293T-TetR cells with linearised or supercoiled single plasmids and/or modular constructs encoding the producer LV components (HIV-1 GFP genome, HIV-1 inducible GagPol, HIV-1 inducible Rev and inducible envelope (VSV-G)) using Lipofectamine™ 2000 CD. Forty-eight hours post-transfection the media was replaced with condition media containing the relevant antibiotic(s) (e.g Zeocin™, hygromycin, blasticidin) for selection of cells containing the required integrated nucleic acid sequences. When the producer cell line pools had recovered from selection, they were cultured for 2 weeks prior to screening for LV productivity.

Retroviral Vector Production by Plasmid Transient Co-Transfection of HEK293T Cells Vector DNA was transfected into HEK293T cells or HEK293T.TetR cells in 10 cm plates that had been pre-seeded with 3.5×10⁶ cells approximately 18 hours prior to transfection. Plasmid DNAs were transfected into the cells using Lipofectamine 2000CD. Sodium butyrate was added approximately 6 hours post-transfection at 10 mM final concentration. Vector-containing harvest supernatant 1 (H1) was taken 16-18 hours later followed by a second harvest (H2) 24 hours later. Vector production was also produced in smaller scale multiwell plates (e.g. 6-well plates) and in this instance the 10 cm vector production protocol was scaled down according to surface area ratios. Vector harvest supernatants were filtered through 0.45 μm filters and stored at −80° C. prior to vector titration assays. GFP-encoding vectors were titrated by transduction of target cells and analysis 3 days later by GFP FACS assay.

In addition to the standard procedure outlined above LV was also generated using the tetracycline-inducible system. In this instance the same procedures as outlined above were followed except that HEK293T-TetR cells were transiently transfected with inducible packaging plasmid DNAs and genome. Each of the packaging plasmids (GagPol, VSV-G, Rev) are driven by CMV promoters into which two copies of the tetracycline operator sequences (TetO2) have been inserted. Following transfection of the plasmid DNAs the tetracycline repressor (TetR) protein, which is constitutively expressed by the HEK293T-TetR cells, binds to the TetO2 sequences in the packaging plasmids and physically blocks transcription from the upstream CMV promoter. Therefore, production of LV cannot occur until the expression of the packaging components has been switched on. This involves the addition of an inducing agent (tetracycline or its analogue doxycycline [dox]), as this binds to the TetR homodimers, causing allosteric changes such that it can no longer bind to the TetO2 sequences, and gene expression of the packaging components is switched on. Therefore, in addition to the above procedures an inducing step was further performed where Doxycycline was added post-transfection at a final concentration of 1 μg/ml.

Retroviral Vector Production from Packaging Cell Lines

Vector production from packaging cells (pools of cells and clones) was performed as described above but only genome plasmid was transfected. When induction with doxycycline was required it was added post transfection at a final concentration of 1 μg/ml.

Retroviral Vector Production from Producer Cell Lines

Six-well plates were seeded with pools of producer cell lines at a density of 2E+06 cells per well, in triplicate. Approximately 24 hours later the pools of producer cells were induced with doxycycline (1 μg/ml final concentration) and Sodium Butyrate (10 mM final concentration). Vector-containing harvest supernatant 1 (H1) was taken 16-18 hours later followed by a second harvest (H2) 24 hours later. Vector from harvest 2 was quantified by GFP FACS assay.

SDS-PAGE and Immunoblotting

Standard SDS-PAGE and Immunoblotting protocols were carried out primarily on End-of-vector production cells, post vector harvest. Approximately 1E+06 end-of-vector production cells were lysed in 200 μL fractionation buffer (0.1 M Tris.Cl, pH7.3, 0.2% [v/v] Nonidet P40) and the nuclei removed by centrifugation, lysis volumes were adjusted if lower cell numbers were harvested. Protein samples were quantified by BioRad assay and typically 10 μg of protein was loaded onto pre-formed, 12-15 well, 4-20% acrylamide gels. Proteins were transferred to nitrocellulose membrane using the Bio-Rad Trans-Blot Turbo Transfer System according to manufacturer's instructions. Blots were blocked in blocking buffer (5% milk PBS/tween-20) overnight at 4° C. Blots were probed with primary antibodies and HRP-secondary antibodies at typically 1:1000 dilution in blocking buffer. Immunoblots were analysed by ECL-detection followed by imaging and analysis using a BioRad ChemiDoc.

Retroviral Vector Quantification Assays

GFP FACS Assay

GFP FACS assay was used to determine vector integration titre by measuring the percentage of transduced cells expressing GFP by flow cytometry. HEK293T cells were seeded in 96-well well plates at a density of 7.5E+03 cells/well. Twenty-four hours later harvested, filtered GFP-encoding vector supernatants were diluted in the range 1:10 to 1:100 in media before 50 μL or each dilution was used to transduce the HEK293T cells in the presence of 8 μg/mL polybrene. If larger scale transductions are performed then the assay is scaled accordingly. Cultures were analysed for GFP expression levels 3 days post transduction using a FACS Verse. Vector titres were calculated according to the percentage GFP positive cells and vector titre reported as transducing units per millilitre (TU/ml).

Product Enhanced Reverse Transcriptase Assay.

Product enhanced reverse transcriptase (PERT) assay measures the amount of RT activity within vector preparations, which is an indirect measure of the functionality of the GagPol construct. The RT associated with vector particles was released by treatment with a mild detergent (particle disruption buffer) and used to synthesise cDNA using MS2 bacteriophage RNA as template. The amount of cDNA resulting is proportional to the amount of RT released from the particles and was quantified using a real-time PCR thermal cycler machine. The number of molecules of cDNA generated by the RT activity represents the relative number of vector particles present. An HIV vector reference standard of known titre was included in each PERT assay and comparison of results from the unknown test vector samples to the vector standard allowed estimation to be made of the actual particle number, and reported as PERT predicted titre in TU per ml (TU/ml).

Various preferred features and embodiments of the present invention will now be described with reference to the following numbered paragraphs.

1. A cell for producing retroviral vectors comprising nucleic acid sequences encoding:
  i) gag-pol;
  ii) env;
  iii) optionally the RNA genome of the retroviral vector; and
  iv) optionally rev, or a functional substitute thereof, wherein at least two nucleic acid sequences are located at the same genetic locus in the genome of the cell; and wherein the at least two nucleic acid sequences are in reverse and/or alternating orientations; and wherein the nucleic acid sequences encoding gag-pol and/or env are associated with at least one regulatory element.

2. A cell for producing retroviral vectors comprising nucleic acid sequences encoding:
  i) gag-pol;
  ii) env;
  iii) optionally the RNA genome of the retroviral vector; and
  iv) rev, or a functional substitute thereof, wherein at least two nucleic acid sequences are located at the same genetic locus in the genome of the cell; and wherein the nucleic acid sequences encoding rev and env are in reverse and/or alternating orientations.

3. A transient production cell for producing retroviral vectors comprising nucleic acid sequences encoding:
   i) gag-pol;
   ii) env;
   iii) optionally the RNA genome of the retroviral vector; and
   iv) rev, or a functional substitute thereof,
   wherein at least two nucleic acid sequences are located at the same genetic locus in the genome of the cell; and wherein the nucleic acid sequences encoding gag-pol and rev are in reverse and/or alternating orientations.

4. The cell according to paragraph 3 wherein the nucleic acid sequences encoding gag-pol and/or env are associated with at least one regulatory element.

5. The cell according to any one of paragraphs 1 to 4, wherein the at least two nucleic acid sequences are any one of the following combinations:
   i) the RNA genome of the retroviral vector and rev, or a functional substitute thereof;
   ii) the RNA genome of the retroviral vector and gag-pol;
   iii) the RNA genome of the retroviral vector and env;
   iv) gag-pol and rev, or a functional substitute thereof;
   v) gag-pol and env;
   vi) env and rev, or a functional substitute thereof;
   vii) the RNA genome of the retroviral vector, rev, or a functional substitute thereof, and gag-pol;
   viii) the RNA genome of the retroviral vector, rev, or a functional substitute thereof, and env;
   ix) the RNA genome of the retroviral vector, gag-pol and env;
   x) gag-pol, rev, or a functional substitute thereof, and env; or
   xi) gag-pol, rev, or a functional substitute thereof, the RNA genome of the retroviral vector, and env.

6. The cell according to any one of the preceding paragraphs, wherein the at least two nucleic acid sequences are located on an extrachromosomal element.

7. The cell according to paragraph 6, wherein the extrachromosomal element is a bacterial plasmid.

8. The cell according to paragraph 6, wherein the extrachromosomal element is either one of these:minicircle DNA, plasmid DNA containing just the regions of interest, DNA generated using an enzymatic DNA amplification platform such as doggybone DNA (dbDNA).

9. The cell according to any one of paragraphs 1 to 5, wherein the at least two nucleic acid sequences are integrated in the cellular genome.

10. The cell according to any one of paragraphs 1 to 9, wherein the cell does not contain a sequence derived from a PAC, BAC, YAC, cosmid or fosmid.

11. The cell according to paragraph 10, wherein the sequence derived from a PAC, BAC, YAC, cosmid or fosmid is an origin of replication.

12. A cell for producing retroviral vectors comprising nucleic acid sequences encoding:
   i) gag-pol;
   ii) env;
   iii) the RNA genome of the retroviral vector; and
   iv) optionally rev, or a functional substitute thereof,
   wherein the nucleic acid sequences are located at, at least, two different loci within the cell, further wherein at least two nucleic acid sequences are located at the same genetic locus in the genome of the cell; and wherein the nucleic acid sequences encoding gag-pol and/or env are associated with at least one regulatory element.

13. A cell for producing retroviral vectors comprising nucleic acid sequences encoding:
   i) gag-pol;
   ii) env;
   iii) optionally the RNA genome of the retroviral vector; and
   iv) rev, or a functional substitute thereof,
   wherein the nucleic acid sequences are located at, at least, two different loci within the cell, further wherein at least two nucleic acid sequences are located at the same genetic locus in the genome of the cell; and wherein the nucleic acid sequences encoding rev and env are in reverse and/or alternating orientations.

14. The cell according to paragraph 12 or paragraph 13, wherein the at least two nucleic acid sequences are any one of the following combinations:
   i) the RNA genome of the retroviral vector and rev, or a functional substitute thereof;
   ii) the RNA genome of the retroviral vector and gag-pol;
   iii) the RNA genome of the retroviral vector and env;
   iv) gag-pol and rev, or a functional substitute thereof;
   v) gag-pol and env;
   vi) env and rev, or a functional substitute thereof;
   vii) the RNA genome of the retroviral vector, rev, or a functional substitute thereof, and gag-pol;
   viii) the RNA genome of the retroviral vector, rev, or a functional substitute thereof, and env;
   ix) the RNA genome of the retroviral vector, gag-pol and env; or
   x) gag-pol, rev, or a functional substitute thereof, and env.

15. The cell according to any one of paragraphs 12 to 14, wherein the at least two nucleic acid sequences are in reverse and/or alternating orientations.

16. The cell according to paragraphs 12 to 15, wherein one of the loci is located on an extrachromosomal element.

17. The cell according to paragraph 16, wherein the extrachromosomal element is a bacterial plasmid.

18. The cell according to paragraph 16, wherein the extrachromosomal element is either one of these:
   minicircle DNA, plasmid DNA containing just the regions of interest, DNA generated using an enzymatic DNA amplification platform such as doggybone DNA (dbDNA).

19. The cell according to any one of paragraphs 12 to 18 wherein the cell does not contain a sequence derived from a PAC, BAC, YAC, cosmid or fosmid.

20. The cell according to paragraph 19, wherein the sequence derived from a PAC, BAC, YAC, cosmid or fosmid is an origin of replication.

21. The cell according to any of the preceding paragraphs, wherein the cell is a packaging cell 22. The cell according to any of the preceding paragraphs, wherein the cell is a producer cell.

23. The cell according to any of the preceding paragraphs, wherein the retroviral vectors are lentiviral vectors, alpha-retroviral vectors, gamma-retroviral vectors or foamy-retroviral vectors.

24. The cell according to any of the preceding paragraphs, wherein the lentiviral vectors are HIV-1, HIV-2, SIV, FIV, BIV, EIAV, CAEV or Visna.

25. A modular construct comprising at least two nucleic acid sequences selected from nucleic acid sequences encoding:

i) gag-pol;
ii) env;
iii) the RNA genome of the retroviral vector; and
iv) rev, or a functional substitute thereof;
wherein the at least two nucleic acid sequences are in reverse and/or alternating orientations; and wherein:
  a) when the modular construct comprises a nucleic acid sequence encoding gag-pol, said nucleic acid sequence encoding gag-pol is associated with at least one regulatory element; or
  b) when the modular construct comprises a nucleic acid sequence encoding env, said nucleic acid sequence encoding env is associated with at least one regulatory element; or
  c) when the modular construct comprises nucleic acid sequences encoding gag-pol and env, said nucleic acid sequences encoding gag-pol and env are associated with at least one regulatory element.

26. A modular construct comprising at least two nucleic acid sequences selected from nucleic acid sequences encoding:
  i) gag-pol;
  ii) env;
  iii) the RNA genome of the retroviral vector; and
  iv) rev, or a functional substitute thereof;
wherein the modular construct does not contain a sequence derived from a PAC, BAC, YAC, cosmid or fosmid; and wherein:
  a) when the modular construct comprises a nucleic acid sequence encoding gag-pol, said nucleic acid sequence encoding gag-pol is associated with at least one regulatory element; or
  b) when the modular construct comprises a nucleic acid sequence encoding env, said nucleic acid sequence encoding env is associated with at least one regulatory element; or
  c) when the modular construct comprises nucleic acid sequences encoding gag-pol and env, said nucleic acid sequences encoding gag-pol and env are associated with at least one regulatory element.

27. A modular construct comprising nucleic acid sequences encoding env and rev, or a functional substitute thereof, in reverse and/or alternating orientations, and optionally nucleic acid sequences encoding gag-pol and/or the RNA genome of the retroviral vector.

28. A modular construct comprising nucleic acid sequences encoding env and rev, or a functional substitute thereof, in reverse and/or alternating orientations, and optionally nucleic acid sequences encoding gag-pol and/or the RNA genome of the retroviral vector, wherein the modular construct does not contain a sequence derived from a PAC, BAC, YAC, cosmid or fosmid.

29. The modular construct according to paragraph 26 or paragraph 28, wherein the sequence derived from a PAC, BAC, YAC, cosmid or fosmid is an origin of replication.

30. The modular construct according to any one of paragraphs 25 to 29, wherein the modular construct is a bacterial plasmid.

31. The modular construct according to any one of paragraphs 25 to 30, wherein the vector is either one of these:
  minicircle DNA, plasmid DNA containing just the regions of interest, DNA generated using an enzymatic DNA amplification platform such as doggybone DNA (dbDNA).

32. The modular construct according to any one of paragraphs 25 to 31, wherein the at least two nucleic acid sequences are any one of the following combinations:

i) the RNA genome of the retroviral vector and rev, or a functional substitute thereof;
  ii) the RNA genome of the retroviral vector and gag-pol;
  iii) the RNA genome of the retroviral vector and env;
  iv) gag-pol and rev, or a functional substitute thereof;
  v) gag-pol and env;
  vi) env and rev, or a functional substitute thereof;
  vii) the RNA genome of the retroviral vector, rev, or a functional substitute thereof, and gag-pol;
  viii) the RNA genome of the retroviral vector, rev, or a functional substitute thereof, and env;
  ix) the RNA genome of the retroviral vector, gag-pol and env;
  x) gag-pol, rev, or a functional substitute thereof, and env; or
  xi) gag-pol, rev, or a functional substitute thereof, the RNA genome of the retroviral vector, and env.

33. A cell for producing retroviral vectors comprising at least one modular construct of any one of paragraphs 26 to 32.

34. The cell according to paragraph 33 wherein the cell is a stable packaging cell.

35. The cell according to paragraph 33 wherein the cell is a stable producer cell.

36. The cell according to any one of paragraphs 1 to 24 or paragraphs 33 to 35 or the modular construct according to any one of paragraphs 25 to 32, wherein the nucleic acid sequences are associated with at least one transcription regulation element.

37. The cell or modular construct according to paragraph 36 wherein the transcription regulation element is selected from the tetracycline repressor (TetR) group of transcription regulators, such as T-Rex, Tet-On and Tet-Off.

38. The cell or modular construct according to paragraph 36 wherein the transcription regulation element is selected from the cumate inducible switch system transcription regulators, such as cumate repressor (CymR) protein.

39. The cell according to any one of paragraphs 1 to 24 or paragraphs 33 to 35 or the modular construct according to any one of paragraphs 25 to 32, wherein the nucleic acid sequences are associated with at least one translation repression element.

40. The cell or modular construct according to paragraph 39, wherein the translation repression element is a tryptophan-activated RNA-binding protein (TRAP).

41. The cell or modular construct according to paragraph 36, wherein the transcription regulation element is a promoter.

42. The cell or modular construct according to paragraph 36, wherein the transcription regulation element is a CMV promoter.

43. The cell or modular construct according to paragraph 36, wherein the transcription regulation element is an enhancer.

44. The cell or modular construct according to paragraph 36, wherein the transcription regulation element is an IRES.

45. The cell according to any one of paragraphs 1 to 24 or paragraphs 33 to 35 or the modular construct according to any one of paragraphs 25 to 32, wherein the nucleic acid sequences are associated with at least one insulator.

46. A method for generating a production cell for producing retroviral vectors, comprising the steps of:
  a) introducing at least one modular construct according to any one of paragraphs 25 to 33 or 37 to 45 into a mammalian cell; and b) optionally selecting for a mammalian cell which has the at least two nucleic acid sequence integrated within its genome.

47. A stable cell for producing retroviral vectors produced by the method according to paragraph 46.

48. A transient cell for producing retroviral vectors produced by the method according to paragraph 46.

49. A method for producing a replication defective retroviral vector, comprising the steps of:
 a) introducing a modular construct according to any one of paragraphs 25 to 33 or 37 to 45 into a mammalian cell;
 b) selecting for a mammalian cell which has the at least two nucleic acid sequence integrated within its genome;
 c) optionally introducing a nucleic acid vector which is different to the modular construct into the selected mammalian cell; and
 d) further culturing the mammalian cell under conditions in which the replication defective retroviral vector is produced.

50. A method for producing a replication defective retroviral vector, comprising the steps of:
 a) introducing a modular construct according to any one of paragraphs 25 to 33 or 37 to 45 into a mammalian cell;
 b) optionally introducing a nucleic acid vector which is different to the modular construct into the mammalian cell; and
 c) further culturing the mammalian cell under conditions in which the replication defective retroviral vector is produced.

51. The method according to paragraph 49 or 50, further comprising the step of isolating the replication defective retroviral vector.

52. The method according to any one of paragraphs 46 or 49 to 51, wherein the nucleic acid vector comprises at least one nucleic acid sequence selected from nucleic acid sequences encoding:
 i) gag-pol;
 ii) env;
 iii) the RNA genome of the retroviral vector; or
 iv) rev, or a functional substitute thereof,
 which are not present on the modular construct.

53. The method according to any one of paragraphs 46 or 49 to 52 wherein the modular construct and/or nucleic acid vector is introduced into the cell by transfection.

54. The method according to paragraph 46 or 49 to 52 wherein the modular construct and/or nucleic acid vector is introduced into the cell by electroporation.

55. A replication defective retroviral vector produced by the method according to any one of paragraphs 46 or 49 to 54.

The invention claimed is:

1. A bacterial plasmid comprising nucleic acid sequences encoding env and rev in reverse orientations, wherein the nucleic acid sequences encoding env and rev are each operably linked to at least one transcription regulation element selected from the tetracycline repressor (TetR) group of transcription regulators or from the cumate inducible switch system transcription regulators.

2. The bacterial plasmid according to claim 1, further comprising a nucleic acid sequence encoding gag-pol.

3. The bacterial plasmid according to claim 1, wherein the bacterial plasmid comprises nucleic acid sequences encoding any one of the following combinations:
 i) an RNA genome of a retroviral vector, rev and env; or
 ii) gag-pol, rev, an RNA genome of a retroviral vector, and env.

4. The bacterial plasmid according to claim 3, wherein the bacterial plasmid comprises nucleic acid sequences encoding gag-pol, rev, the RNA genome of the retroviral vector, and env.

5. A cell comprising at least one bacterial plasmid according to claim 1, wherein the bacterial plasmid is stably integrated within the genome of the cell.

6. A cell comprising a retroviral vector comprising nucleic acid sequences encoding:
 i) gag-pol;
 ii) env;
 iii) rev, and
 iv) optionally, the RNA genome of the retroviral vector;
 wherein the nucleic acid sequences encoding rev and env are located at the same genetic locus; wherein the nucleic acid sequences encoding rev and env are in reverse orientations; wherein the nucleic acid sequences encoding rev and env are stably integrated into the genome of the cell; and wherein the nucleic acid sequences encoding env and rev are each operably linked to at least one transcription regulation element selected from the tetracycline repressor (TetR) group of transcription regulators or from the cumate inducible switch system transcription regulators.

7. The cell according to claim 6, wherein the nucleic acid sequences located at the same genetic locus are any one of the following combinations:
 i) env and rev;
 ii) the RNA genome of the retroviral vector, rev, and env;
 iii) gag-pol, rev and env; or
 iv) gag-pol, rev, the RNA genome of the retroviral vector, and env.

8. The cell according to claim 6, wherein the cell is a packaging cell or a producer cell.

9. The cell according to claim 7, wherein the cell is a packaging cell or a producer cell.

10. A cell comprising at least one bacterial plasmid according to claim 4, wherein the cell is a stable packaging cell or a stable producer cell.

11. A bacterial plasmid comprising nucleic acid sequences encoding env, rev, and gag-pol, wherein the nucleic acid sequences encoding env and rev are in reverse orientations to one another; and wherein the nucleic acid sequences encoding env, rev, and gag-pol are each operably linked to at least one transcription regulation element selected from the tetracycline repressor (TetR) group of transcription regulators or from the cumate inducible switch system transcription regulators.

12. The bacterial plasmid according to claim 11, further comprising an RNA genome of a retroviral vector.

* * * * *